(12) United States Patent
Evans et al.

(10) Patent No.: US 10,201,544 B2
(45) Date of Patent: Feb. 12, 2019

(54) METHOD OF SYNTHESISING ADCS USING AFFINITY RESINS

(71) Applicant: ADC Biotechnology Ltd., St. Asaph (GB)

(72) Inventors: David J. Evans, Chester (GB); Colin M. McKee, Conwy (GB)

(73) Assignee: ADC Biotechnology Ltd., St. Asaph (GB)

( * ) Notice: Subject to any disclaimer, the term of this patent is extended or adjusted under 35 U.S.C. 154(b) by 18 days.

(21) Appl. No.: 14/786,387

(22) PCT Filed: Apr. 25, 2014

(86) PCT No.: PCT/GB2014/051304
§ 371 (c)(1),
(2) Date: Oct. 22, 2015

(87) PCT Pub. No.: WO2014/174316
PCT Pub. Date: Oct. 30, 2014

(65) Prior Publication Data
US 2016/0067352 A1 Mar. 10, 2016

(30) Foreign Application Priority Data
Apr. 26, 2013 (GB) .................................. 1307574.2

(51) Int. Cl.
| A61K 47/48 | (2006.01) |
| A61K 31/5365 | (2006.01) |
| A61K 38/05 | (2006.01) |
| C07K 16/28 | (2006.01) |
| C07K 16/40 | (2006.01) |
| A61K 47/68 | (2017.01) |

(52) U.S. Cl.
CPC .......... *A61K 31/5365* (2013.01); *A61K 38/05* (2013.01); *A61K 47/6803* (2017.08); *A61K 47/6849* (2017.08); *A61K 47/6855* (2017.08); *C07K 16/2863* (2013.01); *C07K 16/40* (2013.01)

(58) Field of Classification Search
CPC .......................... A61K 47/48; A61K 47/48646
USPC ................................... 424/197.11
See application file for complete search history.

(56) References Cited

U.S. PATENT DOCUMENTS

| 2002/0197694 A1 | 12/2002 | Shao |
| 2005/0276812 A1 | 12/2005 | Ebens et al. |
| 2009/0286258 A1 | 11/2009 | Kaur et al. |
| 2011/0046353 A1 | 2/2011 | Liddell |

FOREIGN PATENT DOCUMENTS

| CN | 1993146 A | 7/2007 |
| CN | 102056943 A | 5/2011 |
| CN | 102858798 A | 1/2013 |
| JP | 2011/521909 A | 7/2011 |
| WO | WO-2004/035199 A1 | 4/2004 |
| WO | WO-2005/039641 A2 | 5/2005 |
| WO | WO-2005/117986 A2 | 12/2005 |
| WO | WO-2009/117531 A1 | 9/2009 |
| WO | WO-2009/138714 A1 | 11/2009 |
| WO | WO-2011/109308 A1 | 9/2011 |
| WO | WO-2012/140433 A1 | 10/2012 |
| WO | WO-2012/163805 A1 | 12/2012 |

OTHER PUBLICATIONS

Zamolo et al. (J. Phys. Chem. B, 2010, 114: 9367-9380).*
Dev Baines (ProMetic BioSciences, Jun. 27, 2007, pp. 1-49).*
Roque, A. C. A. et al., "Antibodies and Genetically Engineered Related Molecules: Production and Purification", *Biotechnology Progress*, 20(3):639-654 (American Institute of Chemical Engineers, USA, Jan. 30, 2004).
International Search Report from parent PCT application PCT/GB2014/051304 dated Aug. 7, 2014.
Kabir, S., "Immunoglobin Purification by Affinity Chromatography Using Protein A Mimetic Ligands Prepared by Combinatorial Chemical Synthesis", *Immunological Investigations*, 31(3-4):263-278 (2002).
Qian, J. et al., "A synthetic Protein G adsorbent based on the multi-component Ugi reaction for the purification of mammalian immunoglobins", *Journal of Chromatography B*, 898:15-23 (2012).
Written Opinion from parent PCT application PCT/GB2014/051304 dated Apr. 7, 2015.
Search Report from GB1307574.2 dated Oct. 25, 2013.
Bywater et al., "Desorption of immunoglobulins from Protein A-Sepharose CL-4B under mild conditions," J Immunol Methods, 64(1-2):1-6 (1983).
Pigeon et al., "Application of Fabsorbent™ F1P HF, a Synthetic Ligand Adsorbent for Capture and Purification of a Single-Domain Antibody Fragment Expressed in *Escherichia coli*," Bioprocess International, 7(7):90-91 (2009).
Rocque et al., "An artificial protein L for the purification of immunoglobulins and Fab fragments by affinity chromatography," J Chromatogr A, 1064(2):157-67 (2005).
Teng et al., "Affinity chromatography on immobilized 'biomimetic' ligands: synthesis, immobilization and chromatographic assessment of an immunoglobulin G-binding ligand," J Chromatogr B Biomed Sci Appl, 740(1):1-15 (2000).

* cited by examiner

*Primary Examiner* — Yan Xiao
(74) *Attorney, Agent, or Firm* — Foley Hoag LLP; Dana M. Gordon; Alexander J. Chatterley

(57) ABSTRACT

This invention relates to a solid phase method of synthesizing biomolecule-drug conjugates. In particular, this invention relates to a solid phase method of synthesizing antibody-drug conjugates (ADCs). This invention also relates to intermediate methods of producing immobilized, chemically modified biomolecules, e.g. antibodies. The invention also relates to various uses of capture resins and to biomolecule-drug conjugates, intermediate products and compositions prepared by the methods of the invention.

26 Claims, 6 Drawing Sheets

METHOD OF SYNTHESISING ADCS USING AFFINITY RESINS

RELATED APPLICATIONS

This application is the U.S. national phase of International Patent Application No. PCT/GB2014/051304, filed Apr. 25, 2014, which claims priority to United Kingdom Patent Application serial number GB 1307574.2, filed Apr. 26, 2013.

This invention relates to a solid phase method of synthesising biomolecule-drug-conjugates. In particular, this invention relates to a solid phase method of synthesising antibody-drug-conjugates (ADCs). This invention also relates to intermediate methods of producing immobilised, chemically modified biomolecules, e.g. antibodies.

In addition to the above methods, the invention relates to various uses of capture resins, biomolecule-drug-conjugates, intermediate products, and compositions of the methods of the invention.

BACKGROUND

Immunotoxins and antibody drug conjugates (ADCs) are proteinaceous drugs combining a target-specific binding domain with a drug molecule of sufficient potent toxicity that it may be classed as cytotoxic. Antibodies are the ideal biomolecule for this purpose creating a targeting system combining high specificity with high antigen affinity allowing the transportation of the cytotoxic drug direct to the site of desired administration. These drug constructs are potentially therapeutic against diseases, finding particular prevalence within oncology.

The main criteria of an Antibody Drug Conjugate (ADC) are that the toxin 'warhead' (drug) has activity at extremely low levels (picoM). Furthermore, it is advantageous to have efficacy towards tumours cells irrespective of the point in the cycle. For this purpose DNA active agents have found favour as toxin candidates as DNA damage, unless repairable, will drive apoptosis irrespective of the point in the cycle.

In principle, a suitable toxin for an ADC can be any moiety defined as a L01 ATC molecule ('Anatomical Therapeutic Chemical Classification System' where L01 is a subgroup defining antineoplastic and immunomodulating agents, defined by WHO Collaborating Centre for Drug Statistics Methodology). Alternatively, other moieties that may be categorised as suitable payloads for ADCs may be simply defined as anything that is toxic to cells once internalised. Most moieties falling in the latter category would lack sufficient potency to be effective. Hence, there is an industry trend to identify and exploit 'ultra-potency' materials.

An expert review on the rationale, design and effectiveness of immunotoxin and ADC research can be found within: J. Adair et al, Expert Opin. Biol. Ther., 2012, 12(9): P1191-206, G. Casi et al, Journal of Controlled Release, 2012, 161, 2, P 422-428 and F. Dosio et al, Toxins, 2011, 3, P 848-883.

A number of solution-phase methods can be used to manufacture biomolecule-drug-conjugates, e.g. antibody-drug-conjugates (ADCs). However, solution phase methods are themselves wasteful in terms of generating large volumes of waste and are problematic in terms of aggregation of the biomolecule-drug-conjugates during synthesis.

The first step in a solution-phase method for manufacturing biomolecule-drug-conjugates generally involves chemical modification or activation of the biomolecule. For example, where the biomolecule is an antibody, the antibody can be 'chemically modified' or 'activated' by reducing or partially reducing the antibody. A suitable process for partial reduction of antibodies is given in "Bioconjugate Techniques", page 96/97, Greg T. Hermanson, Academic Press; 2nd edition, 2008, ISBN-13: 978-0123705013. A reducing agent such as TCEP is generally employed in the reduction process.

After chemical modification or activation of the antibody, e.g. reduction, the next step is to remove any excess activation/chemical modification agent, e.g. excess reducing agent. This step is very time consuming as it is sometimes necessary to run the sample through a separation column multiple times. This can also be problematic in terms of degradation if stability of the biomolecule is an issue. The issue of purification of the chemically modified/activated biomolecule is particularly problematic if the process involves the full reduction of a ThiomAb with a large excess of a reducing agent.

After the above purification step, the chemically modified/activated, e.g. reduced, antibody is then be conjugated with a drug moiety. The major problem with this step is the high probability of aggregation of the biomolecule-drug-conjugate. This is particularly problematic when highly hydrophobic drugs are employed in the process. Aggregation is a major problem as it can lead to unusable biomolecule-drug-conjugates. In the best case scenario, biomolecule-drug-conjugates contaminated with biomolecule-drug-conjugate aggregates must be further purified to remove the aggregates, which is both time consuming and very wasteful. A large proportion of the drug will be lost during purification as it forms part of the aggregated biomolecule-drug-conjugate. In the worst case the entire batch of biomolecule-drug-conjugate contaminated with biomolecule-drug-conjugate aggregate to such a high degree it is entirely unusable and must be disposed of.

Oncologists have been working on harnessing target-specific monoclonal antibodies to deliver cytotoxic drugs to the site of tumors as long as monoclonal antibodies have existed; nearly three decades. Up until now three classes of toxin have dominated the field. Namely, calicheamicins, maytansines and auristatins. These cytotoxic drug classes are all typically hydrophobic in nature. When conjugated to an antibody their presence increases the overall hydrophobicity of the antibody significantly and in some cases to the extent that hydrophobic interactions between conjugates leads to conjugate aggregation. The order of significance of this issue is Calicheamicin>Maytansine>Auristatin based on the knowledge that the processes for both Mylotarg and CMC-544 contain chromatographic aggregate removal steps. Approximately 50% of maytansine processes contain aggregate removal steps and very few auristatin processes contain aggregate removal steps.

More recently, toxins based on duocarmycins (www.syntarga.com) and pyrollebenzodiazepene (PBD) dimers (www.spirogen.com) have been conjugated to antibodies and are undergoing pre-clinical evaluation. These new classes of toxin are even more hydrophobic than their predecessor cytotoxin drug classes and are more prone to aggregation when conjugated to antibodies.

Significant efforts have been focussed on modulation of the hydrophobicity of the drug by incorporating hydrophilic linkers (Zhao et al, J. Med. Chem., 2011, 54, 10, 3606-3623). Where aggregate formation cannot be controlled developers have relied on well-known techniques for aggregate removal from protein based therapeutics. These include a range of different chromatographic separations including ion exchange, hydrophobic interaction, hydroxyapatite and others well known to those in the art. Undertaking such chromatographic purification techniques has the result of achieving adequate product quality but at the expense of process yield. When working with antibodies and antibody based therapeutics in the context of manufacturing physical loss of material through ambiguous, incidental side reactions or unwanted physiochemical interactions has a hugely significant financial impact.

Accordingly, the conventional solution-phase processes for manufacturing biomolecule-drug-conjugate are beset with difficulties and it would be desirable to provide an improved process for manufacturing biomolecule-drug-conjugates.

The present invention addresses one or more of the above issues with the conventional solution-phase methods.

BRIEF SUMMARY OF THE DISCLOSURE

Method of Synthesising a Biomolecule-Drug-Conjugate:

In accordance with the present invention there is provided a method of synthesising a biomolecule-drug-conjugate, the method comprising:
(i) contacting a biomolecule with a capture resin under conditions suitable to immobilise the biomolecule and therefore provide an immobilised biomolecule; wherein the biomolecule is an antibody, modified antibody or antibody fragment; and wherein the capture resin comprises a biomolecule capture moiety selected from the group consisting of: (1) a non-peptide-based, including amino acid-based, Protein A, Protein G or Protein L mimetic, (2) a peptide-based Protein A, Protein G or Protein L mimetic, (3) a nucleotide binding site capture moiety and (4) a glycoprotein capture moiety;
(ii) optionally contacting the immobilised biomolecule with a chemical modification agent or activating agent to provide a chemically modified or activated, immobilised biomolecule;
(iii) contacting the immobilised biomolecule or the chemically modified or activated, immobilised biomolecule with a drug component to form an immobilised biomolecule-drug-conjugate;
(iv) releasing the biomolecule-drug-conjugate from the capture resin.

A key feature of the above method of the invention is that the capture resin employed in the process is able to immobilise the biomolecule in a consistent and reproducible manner. Consistent immobilisation of the biomolecule to the capture resin should result in reduced variation in the resulting biomolecule-drug-conjugate produced by the above method. For example, the variation in the point at which the drug component is attached to the immobilised biomolecule might be reduced, thus leading to a more consistent point of attachment between the drug component and the immobilised biomolecule. Such an improvement in regio-specificity would be desirable in terms of improving the consistency of the resulting biomolecule-drug-conjugate product.

The employment of a non-peptide-based Protein A, Protein G or Protein L mimetic or a peptide-based Protein A, Protein G or Protein L mimetic (i.e. (1) or (2) in the first step of the above method) as the biomolecule capture moiety, as opposed to the employment of the parent Protein A, Protein G or Protein L as the biomolecule capture moiety, may lead to a relative improvement in consistency in the immobilisation of the biomolecule due to increased regio-specificity of the mimetic verses the conventional Protein A, Protein G or Protein L based systems. In cases in which the regio-specificity of the immobilisation of biomolecules to proteins is low, the employment of the parent Protein A, Protein G or Protein L as the biomolecule capture moiety would inherently result in variable immobilisation of the biomolecule to the capture resin. For example, the parent Protein A, Protein G or Protein L may exhibit non-specific binding via other sites on the protein which may complicate the overall interaction. As explained above, consistent immobilisation of the biomolecule to the capture resin as is envisaged in the present invention may then result in reduced variation in the resulting biomolecule-drug-conjugate produced by the above method. This would be advantageous. Another advantage of the resin systems of the present invention resides in the fact that a wider range of drugs can in principle be conjugated to the resin than is the case for conventional Protein A, Protein G or Protein L based systems. For example, in the case of hydrophobic molecules other non-specific binding that may occur in parent Protein A, Protein G or Protein L based systems may disrupt or prevent effective conjugation of such drugs.

Similar benefits exist for the employment of a nucleotide binding site capture moiety or a glycoprotein capture moiety (i.e. (3) or (4) in the first step of the above method) as the biomolecule capture moiety.

In an embodiment, the capture resin is a non-proteinaceous capture resin. In an embodiment, the biomolecule capture moiety of the capture resin has a molecular weight of about 1000 Da or less, optionally about 500 Da or less, about 300 Da or less or about 200 Da or less. In an embodiment, the capture resin is a non-proteinaceous capture resin and the biomolecule capture moiety of the capture resin has a molecular weight of about 1000 Da or less.

Another benefit of employing a non-peptide-based Protein A, Protein G or Protein L mimetic or a peptide-based Protein A, Protein G or Protein L as the biomolecule capture moiety, as opposed to the employment of the parent Protein A, Protein G or Protein L as the biomolecule capture moiety is that the mimetic biomolecule capture moieties are compatible with a broad range of common antibody conjugation chemistries and can be scaled up to industrial levels. This is in contrast with Protein A, Protein G or Protein L based biomolecule capture moieties.

For example, it is often desirable to target the lysyl side chain functional group on the immobilised antibody. Of the 28 antibody drug conjugates currently in clinical development almost half (those shaded grey in the table below) employ lysine directed conjugation chemistry. The proteinaceous nature of an immobilizing ligand on the surface of Protein A, G or L will result in the unintentional targeting of the lysyl side chain functional groups on the protein capture resin. Protein A (swiss-prot P02976) has 59 Lysine residues, Protein G (swiss-prot P919909) has 59 lysine residues and Protein L (swiss-prot Q51918) has 132 lysine residues.

| Name | Target | Drug + Linker | Developer | Phase | Indication |
| --- | --- | --- | --- | --- | --- |
| ADCetris | CD30 | vcE | Seattle Genetics | MA 2011 | HL and ALCL |

-continued

| Name | Target | Drug + Linker | Developer | Phase | Indication |
|---|---|---|---|---|---|
| CR011-vcE | GPNMB | vcE | Celldex | Ph II | Breast, Melanoma |
| PSMA ADC | PSMA | vcE | Progenics | Ph II | Prostate |
| RG7593 | CD22 | vcE | GNE/Roche | Ph II | Hematological |
| RG7596 | CD79b | vcE | GNE/Roche | Ph II | Hematological |
| SGN-75 | CD70 | mcMMAF | Seattle genetics | Ph 1b | NHL, RCC |
| AGS-5ME | SLC44A4 | vcE | Agensys | Ph I | Prostate, Pancreatic |
| AGS-22ME | Nectin 4 | vcE | Agensys | Ph I | Solid Tumors |
| AGS-16M8F | ENPP3 | mcMMAF | Agnsys | Ph I | Renal Cell Carcinoma |
| BAY 79-4620 | MN/CA-9 | vcE | Bayer | Ph I | Solid Tumors |
| MLN064 | GCC | vcE | Takeda/Millenium | Ph I | Gastrointestinal |
| RG7450 | STEAP 1 | vcE | GNE/Roche | Ph I | Prostate |
| RG7458 | MUC16 | vcE | GNE/Roche | Ph I | Ovarian |
| RG7598 | ? | Auristatin | GNE/Roche | Ph I | Multiple Myeloma |
| RG7599 | ? | Auristatin | GNE/Roche | Ph I | NSCLC, Ovarian |
| RG7600 | ? | Auristatin | GNE/Roche | Ph I | Pancreatic, Ovarian |
| RG7636 | ? | Auristatin | GNE/Roche | Ph I | Melanoma |
| Kadcyla | Her2 | SMCC DM1 | GNE/Roche | MA 2013 | Breast Cancer |
| Lorvotuzumab | CD56 | SPP-DM1 | Immunogen | Ph II | MM, Merkel Cell |
| SAR3419 | CD19 | SPDB-DM4 | Sanofi Aventis | Ph II | NHL, B-ALL |
| SAR566658 | CA6 | SPDB-DM4 | Sanofi Aventis | Ph I | Breast, Ovarian |
| BT-062 | CD138 | SPDB-DM4 | Biotest | Ph I | Multiple Myeloma |
| IMGN-529 | CD37 | SPDB-DM4 | Immunogen | Ph I | NHL |
| IMG-853 | FoIR1 | SPDB-DM4 | Immunogen | Ph I | Ovarian NSCLC |
| BAY-94-9343 | Mesothelin | SPDB-DM4 | Bayer | Ph I | Meso tumors |
| AMG-595 | EGFRvIII | DM1 | Arngen | Ph I | Recurrent Glioma |
| AMG-172 | ? | DM1 | Amgen | Ph I | Renal Cancer |
| CMC-544 | CD22 | Calicheamicin | Pfizer | Ph III | B-cell ALL |

In addition to the competition between ligand and antibody lysyl residues as described above, there are also other issues with Protein A, G and L based capture resins. These include leaching of the protein and immunogenicity of leached adducts. This means that these affinity supports cannot be employed (for purification or conjugation) towards the end of a manufacturing process. Any conjugate material furnished from such a process employing Protein A, G and L based capture resins will not meet current regulatory guidelines for antibody purification and product quality.

Method of Synthesising a Chemically Modified an Activated, Immobilised Biomolecule:

In accordance with the present invention there is provided a method of synthesising a chemically modified or an activated, immobilised biomolecule, the method comprising:
(i) contacting a biomolecule with a capture resin under conditions suitable to immobilise the biomolecule and therefore provide an immobilised biomolecule; wherein the biomolecule is an antibody, modified antibody or antibody fragment; and wherein the capture resin comprises a biomolecule capture moiety selected from the group consisting of: (1) a non-peptide-based, including amino acid-based, Protein A, Protein G or Protein L mimetic, (2) a peptide-based Protein A, Protein G or Protein L mimetic, (3) a nucleotide binding site capture moiety and (4) a glycoprotein capture moiety; and
(ii) contacting the immobilised biomolecule with a chemical modification agent or activating agent to provide a chemically modified or activated, immobilised biomolecule.

Conjugation of proteins and more specifically antibodies is often used in research, diagnostics and therapeutics. Bioconjugate Techniques, Second Edition (Greg T Hermanson) provides highly detailed information on the chemistry, reagent systems and practical applications for creating labelled or conjugate molecules. It also describes dozens of reactions with details on hundreds of commercially available reagents and the use of these reagents for modifying or crosslinking peptides and proteins, sugars and polysaccharides, nucleic acids and oligonucleotides, lipids, and synthetic polymers. A brief summary of key conjugation chemistries applied to antibodies is provided below.

Conjugation to free thiols after reduction of the native interchain disulphides is a common approach to antibody conjugation and the chemistry employed for the commercial ADC ADCetris®. A process comprises contacting the antibody with a reductant such as TCEP, DTT, merceptoethylamine or other suitable reductant well known in the field followed by conjugation with a drug, ligand, label of the formula D-X, where D is the drug, ligand or label and X is a reactive group selected from maleimides, haloalkanes, pyridyl disulphides and other thiol reactive chemistries known in the art.

An alternative approach to thiol conjugation with antibodies is to engineer reactive cysteine residues at specific sites in antibodies to allow drugs to be conjugated with defined stoichiometry without disruption of interchain disulphide bonds. The engineered cysteines are often present as mixed disulphides of cysteine or glutathione. The adducts are removed by complete reduction followed by diafiltration. This breaks the interchain disulphides which must be reformed by oxidation with air, $CuSO_4$ or dehydroascorbic acid.

Another common site for conjugation are amino groups present on the side-chain of lysine residues. The simplest approach comprises contacting the antibody with a drug, ligand, label or linker of the formula D-Y. D has the same definition as above and Y is a reactive group selected from isocyanates, NHS esters, sulfonyl chlorides, epoxides and other reagents known to those skilled in the art.

Indirect conjugation to lysines is often also employed. The amino group of the lysine side chain is first activated with a heterobifunctional linker before this is conjugated with a drug containing a complimentary reactive chemistry.

Examples of such couplets include modification of the lysine with 2-iminothiolane to create a new thiol followed by conjugation with any of the thiol reactive drug-linkers (D-X) described above. Another couplet is the modification of lysine with SMCC to create a lysine bound maleimide followed by conjugation with a drug containing a free thiol. For a complete review of potential couplets useful for indirect lysine conjugation see Hermanson and the Perbio cross-linking agent catalogue.

Several groups have developed ways to incorporate non-natural amino acids with side chains that are chemically orthogonal to the 20 proteogenic amino acid side chains in proteins.

Redwood Bioscience (www.redwoodbioscience.com) has developed a technology they call Aldehyde Tagging. In this they exploit a natural enzyme called formyl glycine enzyme (FGE) which normally converts a Cys residue within a highly conserved 13 amino acid sequence into a formyl glycine (aldehyde) in Type I sulfatases (Wu et al, PNAS, 2009, 106, 9, 3001). Drugs, ligands or labels to be conjugated to such modified antibodies must contain aldehyde reactive chemistries such as oxyamines or hydrazines. A full disclosure of aldehyde reactive functionalities can be found in Hermanson and Perbio catalogues.

Ambryx has developed a technology they call EuCode (Liu et al, Anu. Rev. Biochem., 2010, 79, 413). EuCode is a platform whereby cells are engineered to incorporate non-natural amino acids in heterologous proteins by inclusion of three non-natural components in the expression system:
1. A non-natural amino acid supplemented into the medium
2. An orthogonal aminoacyl-tRNA synthetases (aaRS)
3. An orthogonal tRNA The orthogonal aaRS/tRNA pair has been engineered/selected to promote read through at the amber stop codon and to incorporate the non-natural amino acid at that position. As many as 70 nnAAs have been incorporated into protein using this approach. FIG. 5 expands on the possible combination of orthogonal amino acid side chain and reactive chemistry (adapted from Ambryx presentation at Hanson Wade ADC summit meeting in February 2012).

Sutro has described the production of antibodies and cytokines using an open, cell-free synthesis (OCFS) technology. A feature of OCFS is the ability to incorporate non-natural amino acids into the protein with charged tRNAs that can be directed to a specific codon to deliver the non-natural amino acid to a specific location on the protein—making the protein amenable to specific modification or imparting a new desired property (Goerke et al, Biotechnol. Bioeng., 2008, 99: 351-367).

Immobilized antibody conjugation is compatible with all non-natural amino acid side chains and complimentary reactive chemistries with one proviso. The antibody capture ligand must not contain the novel chemistry incorporated as part of the non-natural amino acid side chain.

Oxidation of polysaccharide residues in glycoproteins with sodium periodate provides a mild and efficient way of generating reactive aldehyde groups for subsequent conjugation with amine or hydrazide containing molecules; drugs, ligands or labels. The process involve first contacting the antibody with sodium periodate and then conjugating with reactive groups selected from amines, hydrazides, aminoxy or other aldehyde reactive chemistries known in the art.

Step (i):

In an embodiment, the step of contacting the biomolecule with the capture resin comprises incubating the biomolecule with the capture resin.

The incubation may be carried out at temperature of from about 0 to about 100° C., preferably at temperature of from about 5 to about 50° C. and optionally at temperature of from about 10 to about 40° C. Ideally, the incubation is carried out at temperature of from about 15 to about 37° C., e.g. the incubation is carried out at room temperature, such as about 21° C. Alternatively, the incubation is carried out at about 37° C.

The incubation may be carried out for a period of time of from about 1 minute to about 3 days, e.g. for a period of time of from about 10 minutes to about 18 hours. Preferably the incubation is carried out for a period of time of from about 20 minutes to about 1 hour.

In an embodiment, the incubation is carried out in an aqueous media. In an alternate embodiment, the incubation is carried out in a buffer solution such as phosphate buffered saline (PBS) or any buffering salt compatible with the desired binding pH and chemistry, optionally the incubation is carried out in a buffer solution such as phosphate buffered saline (PBS). In an embodiment, the incubation is carried out using a co-solvent including a solvent such as DMSO or DMF. The co-solvent may be present within a range of 0.5-80% v/v, such as 0.5-50% v/v.

In an embodiment, the incubation is carried out at a pH of from about 5 to about 10, preferably about 5 to about 8, more preferably about 6 to about 8 In a preferred embodiment, the incubation is carried out at a pH of about 6 to about 7.5, ideally at pH of about 6.5. In another preferred embodiment, the incubation is carried out at a pH of about 7 to about 8, ideally at pH of about 7.4. This results in improved binding of the antibody to the derivatised support.

In an embodiment, the immobilised biomolecule (i.e. the biomolecule that is immobilised on the capture resin) is washed to remove any biomolecule that has not been immobilised on the capture resin. The washing of the immobilised biomolecule can be affected by rinsing with fresh solvent. For example, the washing of the immobilised biomolecule can be affected by rinsing with a buffer solution such as PBS. Optionally, the rinsing of the immobilised biomolecule is carried out in the presence of a chelating agent, such as EDTA. Alternatively, the washing of the immobilised biomolecule can be affected by rinsing with a 'Modification Buffer' including a sodium phosphate buffer, NaCl and a chelating agent, such as EDTA.

Step (ii):

In an embodiment, the step of contacting the immobilised biomolecule with a chemical modification agent or an activating agent to provide a modified or activated, immobilised biomolecule involves reducing the biomolecule. In an embodiment, the reduction of the biomolecule involves complete reduction. In an embodiment, the reduction of the biomolecule involves partial reduction. In an embodiment, the reduction of the biomolecule involves complete reduction followed by re-oxidation.

In an embodiment, the biomolecule is reduced by contacting it with a reducing agent such as tris(2-carboxyethyl) phosphine (TCEP), dithiothreitol merceptoethylamine or other suitable reductant. Preferably the reducing agent is tris(2-carboxyethyl)phosphine (TCEP).

In an embodiment, the reduced biomolecule is re-oxidised by contacting it with an oxidising agent such as air, $CuSO_4$ or dehydroascorbic acid (DHAA). Preferably the oxidising agent is dehydroascorbic acid (DHAA).

In an embodiment, the process of reducing the biomolecule is carried out in a buffer solution such as phosphate buffered saline (PBS).

In an embodiment, the process of reducing the biomolecule is carried out at a pH of from about 5 to about 10, preferably from about 7 to about 8, preferably about 7.4.

In an embodiment, the process of reducing the biomolecule is carried out in the presence of a chelating agent, such as EDTA.

In an embodiment, the process of reducing the biomolecule involves incubating the biomolecule with the reducing agent for a period of time of from about 20 minutes to about 3 days, optionally, from about 1 hour to about 2 days and further optionally from about 6 hours to about 18 hours.

In an embodiment, the step of contacting the immobilised biomolecule with a chemical modification agent or an activating agent to provide a modified or activated, immobilised biomolecule involves reacting the biomolecule with a cross-linker moiety. For example, the crosslinker moiety could be an amine-to-sulfhydryl crosslinker, e.g. a crosslinker having an NHS-ester and a maleimide reactive group at opposite ends. This method of modifying or activating the biomolecule effectively results in a biomolecule-linker-drug-conjugate. Suitable cross-linkers are generally able to react with a primary amine group on the drug (via the reactive NHS ester end) and also react with a cysteine residue on the biomolecule (via the reactive maleimide end). In this particular example, the maleimide end will react with a cysteine in the immobilised biomolecule. An example of such a crosslinker is succinimidyl 4-(N-maleimidomethyl)cyclohexane-1-carboxylate (SMCC).

In an embodiment, the process of reacting with a cross-linker is carried out in a buffer solution such as phosphate buffered saline (PBS). Alternatively, the process of reacting with a crosslinker is carried out in a 'Modification Buffer' including a sodium phosphate buffer, NaCl and a chelating agent, such as EDTA.

In an embodiment, the process of reacting with a cross-linker is carried out at a pH of from about 7 to about 9, preferably from about 7 to about 8, preferably about 8.0.

In an embodiment, the process of reacting with a cross-linker is carried out in the presence of a chelating agent, such as EDTA.

In an embodiment, the process of reacting with a cross-linker involves incubating the biomolecule with the cross-linker for a period of time of from about 20 minutes to about 3 days, optionally, from about 1 hour to about 2 days and further optionally from about 6 hours to about 18 hours.

In an embodiment, the step of contacting the immobilised biomolecule with a chemical modification agent or an activating agent to provide a modified or activated, immobilised biomolecule involves reacting the biomolecule with Traut's reagent.

In an embodiment, the process of reacting with Traut's reagent is carried out in a buffer solution such as phosphate buffered saline (PBS).

In an embodiment, the process of reacting with Traut's reagent is carried out at a pH of from about 7 to about 9, preferably from about 7 to about 8, preferably about 8.0.

In an embodiment, the process of reacting with Traut's reagent is carried out in the presence of a chelating agent, such as EDTA.

In an embodiment, the process of reacting with Traut's reagent involves incubating the biomolecule with the reducing agent for a period of time of from about 20 minutes to about 3 days, optionally, from about 1 hour to about 2 days and further optionally from about 6 hours to about 18 hours.

In an embodiment, the activated, immobilised biomolecule is washed to remove any modification/activating agent. In an embodiment the washing involves rinsing with a buffer, optionally wherein the buffer is phosphate buffered saline (PBS). Other suitable buffers include: Potassium phosphate buffer; Sodium phosphate buffer; Sodium citrate buffer; Bis-Tris propane buffer; HEPES buffer; Sodium acetate buffer; Sodium citrate buffer; Cacodylic acid buffer; Ammonium acetate buffer; Imidazole buffer; Bicine buffer; and 2-(N-morpholino)ethanesulfonic acid (MES) buffer. For example, the immobilised biomolecule can be washed with a buffer solution such as phosphate buffered saline (PBS) at a pH of from about 7 to about 8, preferably about 7.4. Optionally, the rinsing of the activated, immobilised biomolecule is carried out in the presence of a chelating agent, such as EDTA. Another example of rinsing the activated, immobilised biomolecule involves rinsing the resin with a buffer such as PBS followed by a 'Conjugation Buffer' which includes sodium citrate, NaCl and a chelating agent such as EDTA.

Step (iii):

In an embodiment, the step of contacting the chemically modified or activated, immobilised biomolecule with a drug component to form an immobilised biomolecule-drug-conjugate involves contacting the chemically modified or activated, immobilised biomolecule with a drug component in a buffer solution as hereinbefore described with relation to step (ii).

In an embodiment, the step of contacting the chemically modified or activated, immobilised biomolecule with a drug component to form an immobilised biomolecule-drug-conjugate involves contacting the chemically modified or activated, immobilised biomolecule with a drug component at a pH of from about 5 to about 8, preferably about 7 to about 8 and more preferably about 7.4.

In an embodiment, the step of contacting the chemically modified or activated, immobilised biomolecule with a drug component to form an immobilised biomolecule-drug-conjugate is carried out in the presence of a chelating agent, such as EDTA.

In an embodiment, step of contacting the chemically modified or activated, immobilised biomolecule with a drug component to form an immobilised biomolecule-drug-conjugate involves incubating the chemically modified or activated, immobilised biomolecule with drug component for a period of time of from about 20 minutes to about 3 days, optionally, from about 1 hour to about 2 days and further optionally from about 6 hours to about 18 hours.

In an embodiment, the immobilised biomolecule-drug-conjugate is washed prior to the step of releasing the biomolecule-drug-conjugate from the capture resin. The washing removes any unreacted drug component. In an embodiment the washing involves rinsing with a buffer, optionally wherein the buffer is phosphate buffered saline (PBS), and other solvent. Other suitable buffers include: Potassium phosphate buffer; Sodium phosphate buffer; Sodium citrate buffer; Bis-Tris propane buffer; HEPES buffer; Sodium acetate buffer; Sodium citrate buffer; Cacodylic acid buffer; Ammonium acetate buffer; Imidazole buffer; Bicine buffer; and 2-(N-morpholino)ethanesulfonic acid (MES) buffer. For example, the immobilised biomolecule-drug-conjugate can be washed with a buffer solution such as phosphate buffered saline (PBS) and dimethylacetamide (DMA) at a pH of from about 5 to about 7. Optionally, the rinsing of the immobilised biomolecule-drug-conjugate is carried out in the presence of a chelating agent, such as EDTA.

Step (iv):

In an embodiment, the step of releasing the biomolecule-drug-conjugate from the capture resin involves:

a) exposing the support-biomolecule compound to a release agent; and/or
b) altering the pH to break the support-biomolecule bond.

In an embodiment, the release agent is a hydrogen bond disrupter such as co-solvents of Hexafluoroisopropanol, 2,2,2-Trifluoroethanol or dimethylsulfoxide (DMSO).

In an embodiment, the release agent is incubated with the support-biomolecule.

The incubation may be carried out at temperature of from about 0 to about 100° C., preferably at temperature of from about 5 to about 50° C. and optionally at temperature of from about 10 to about 40° C. Ideally, the incubation is carried out at temperature of from about 15 to about 37° C., e.g. the incubation is carried out at room temperature, such as about 21° C. Alternatively, the incubation is carried out at about 37° C.

The incubation may be carried out for a period of time of from about 1 minute to about 3 days. Preferably the incubation is carried out for a period of time of from about 30 minutes to about 2 hours.

The incubation may be carried out in an aqueous media. Alternatively, the incubation may be carried out in a solvent such as DMF, DMSO, MeOH or MeCN. Alternatively, the incubation may be carried out in an aqueous-solvent mixture with up to 80% solvent, preferably 0.5 to 50% and most preferred 0.5% to 10% v/v. In certain cases mixtures of one or more of the above solvents, including water, may be appropriate. Where necessary a stabiliser may also be included to ensure the conjugate remains intact.

In an embodiment, the step of releasing the biomolecule-drug-conjugate from the capture resin involves altering the pH. The pH can be altered by any amount that is sufficient to break the support-biomolecule bond but which will not affect the activity, integrity or 3D structure of the biomolecule.

For example, the pH can be adjusted so that it is acidic. In an embodiment, the pH is decreased from about pH2 to about pH6. Optionally, the pH is adjusted to be less than about pH 5, e.g. about pH 3 to about 5, for example less than about pH 4. In an embodiment, the pH is decreased to about pH 3.

Alternatively, the pH can be adjusted so that it is basic. In an embodiment, the pH is increased to about pH8 to about pH10. Optionally, the pH is adjusted to greater than pH 8. For example, the pH can be increased to about pH 9. The pH can be increased to being greater than pH 9. For example, the pH can be increased to about pH10. The pH can be increased to being greater than pH10, but usually will be less than pH14.

The biomolecule-drug-conjugate may undergo one or more treatments with release agent. Advantageously, the use of a second or subsequent treatment with fresh release agent may result in increasing the amount of biomolecule-drug-conjugate released from the capture resin. Fresh release agent is release agent that has not previously been incubated with the immobilised biomolecule-drug-conjugate.

In an embodiment, the step of releasing the biomolecule-drug-conjugate from the capture resin involves contacting the biomolecule-drug-conjugate with a salt. For example, the biomolecule-drug-conjugate might be contacted with NaCl. The concentration of the salt can range from about 0.1 to about 10M, preferably about 0.1 to about 1M.

In an embodiment, the eluted biomolecule-drug-conjugates is neutralised after the step of releasing the conjugate from the capture resin. For example, the conjugate can be captured into 2% v/v of 1M Tris(hydroxymethyl)aminoethane (TRIS).

Washing Steps:

In an embodiment the step of washing an intermediate in the method of the invention comprises removing substances that are not bound to the capture resin such as contaminants. Typical contaminants include excess reagent used to activate the immobilised biomolecule, biomolecule that has not been immobilised on the capture resin and drug component that has not reacted with the activated, immobilised biomolecule. Any medium that does not affect the activity, integrity or 3D structure of the biomolecule or the integrity of the binding between the immobilised biomolecule and the capture resin can be used to wash the intermediate.

Preferably the buffer is isotonic and induces a stable environment to biomolecules such as antibodies by mimicking physiological pH and ionic strength. In an embodiment, the activated, immobilised biomolecule is washed by filtration. Optionally, the resultant filtrate is buffer-exchanged, e.g. by centrifugation using membrane cartridges.

Typically, additives are introduced to the buffer media. These additives induce a level of control to the buffer system and the biomolecule contained within it. For example, additives such as Tris or histidine are introduced to a buffered process stream to maintain pH and minimise incidental acidification. Typically, the pH of a biomolecule process stream should be maintained between pH5 and 9.5, with the extremes of the pH limits avoided for prolonged periods. Inorganic salts such as 0.1M NaCl(aq) may be added to maintain the ionic strength of the process stream. Ionic and non-ionic detergents such as Tween (polysorbate) may be added to the buffer to favourably increase the solubility of poorly soluble biomolecules in the buffer media and minimise aggregation.

A Mixture Comprising a Capture Resin and an Activating Agent:

In accordance with the present invention there is provided a mixture comprising:
(i) a capture resin comprising an antibody, modified antibody or antibody fragment capture moiety selected from the group consisting of: (1) a non-peptide-based Protein A, Protein G or Protein L mimetic, (2) a peptide-based Protein A, Protein G or Protein L mimetic, (3) a nucleotide binding site capture moiety and (4) a glycoprotein capture moiety; and
(ii) a chemical modification agent or activating agent.

In an embodiment, the capture resin includes an immobilised antibody, modified antibody or antibody fragment on the surface thereof.

A Use of a Capture Resin in the Synthesis of a Biomolecule-Drug-Conjugate:

In accordance with the present invention there is provided a use of a capture resin comprising an antibody, modified antibody or antibody fragment capture moiety selected from the group consisting of: (1) a non-peptide-based Protein A, Protein G or Protein L mimetic, (2) a peptide-based Protein A, Protein G or Protein L mimetic, (3) a nucleotide binding site capture moiety and (4) a glycoprotein capture moiety in the synthesis of a biomolecule-drug-conjugate.

Capture Resin:

For years researchers have tried to develop ligands that have affinity for a range of full length antibodies, fragments or fusions as replacements for traditional Protein A, G or L affinity purification supports. The main criterion for successful ligand discovery/development has been:
1. High selectivity for antibodies to afford high initial purification
2. Useful dynamic binding capacity 3. Elution conditions compatible with retention of antibody integrity
4. Stability of support during multiple elution/cleaning cycles
5. Lowered cost relative to Protein A, G or L supports In the context of using these ligands for solid phase antibody conjugation criterion 1 above is not critical as the conjugation process starts with purified antibody. However, the ligand must meet the remaining 4 criterion in full. In addition, the ligand must ideally have a defined site of interaction with the antibody which affords suitable affinity binding strength for conjugation. This attribute is necessary so that the antibody may be bound to the support and not inadvertently eluted during buffer replenishment over time. In addition, a defined site of interaction is desirable to infer consistent conformational presentation of the bound antibody complex to the surrounding solution phase with the effect of providing a means for consistent and reproducible conjugation chemistry. Antibodies are well characterized biomolecules with a number of well-defined binding domains which are exploited for affinity purification.

The first defined region(s) are the Protein A and Protein G binding pockets which are exploited in affinity chromatography using Protein NG and mimetics of Protein A/G supports. Protein A interacts with the CH2 CH3 interchain domain in the Fc region via number of non-covalent interactions with amino acid residues: Thr 250, Leu 251, Met 252, Ile 253, His 310, Gln 311, Leu 314, Asn 315, Lys 338, Glu 345, Ala 431, Leu 432, His 433, Asn 434 and His 435. Protein A mimetic supports have been rationally designed to interact with this domain via one or more of the amino acids defined above. These mimetic supports afford suitable affinity ligands for IgG binding and conjugation. Protein A mimetic supports may be defined in sub-classes as incorporating non-peptide, peptide or amino acid based ligands. Similarly, Protein G interacts with the CH2 CH3 interchain domain in the Fc region via number of non-covalent interactions with amino acid residues Ile 253, Ser 254, Gln 311, Glu 380, Glu 382, His 433, Asn 434 and His 435. Protein G mimetic supports have been rationally designed to interact with this domain via one or more of the amino acids described above. Once again these mimetic supports afford suitable affinity ligands for IgG binding and conjugation. Protein G mimetic supports may be defined in sub-classes as incorporating non-peptide, peptide or amino acid based ligands. In an embodiment, the capture resin is able to bind to a Protein A or a Protein G binding pocket on a biomolecule.

A second defined region is the antibody light chain as targeted by a Protein L affinity matrix. Protein L binds specifically to Kappa I, II and IV light chains but not Kappa III nor Gamma light chains. The interaction between Protein L with antibodies has been mapped and it was noted that hydrogen bonds and salt bridges are important in binding. A total of 11 hydrophilic amino acid residues—namely; Ala, Asp, Gln, Glu, Gly, Ile, Leu, Lys, Phe, Thr, Tyr—of the Protein L domain are important in forming these bonds. Protein L mimetic affinity supports have been developed by creating triazine scaffold combinatorial libraries using structurally similar chemical compounds to the 11 amino acids disclosed above (WO 2004/035199A). Disclosed within WO2004/035199A a Protein L mimetic is defined as a ligand having 50% of the affinity of Protein L for an antibody or fragment and specificity for the light chain as evidenced by binding of Fab fragments. Any suitable scaffold disclosed herein or known to those skilled in the art can be substituted for the triazine scaffold as long as the characteristics of affinity and specificity for light chain are retained. Such resins are useful for the immobilization of antibodies and fragments containing Kappa I, II and IV light chains. One commercial embodiment of Protein L mimetics is Fabsorbent™ F1P HF (ProMetic Biosciences). This affinity support meets the criterion for a Protein L mimetic but also binds gamma light chain containing antibodies and fragments. Therefore, this affinity support is universally applicable to antibody affinity binding and conjugation. In an embodiment, the capture resin is able to bind to an antibody light chain as targeted by a Protein L affinity matrix.

A third defined region is the conserved nucleotide domain in the Fab arm of all antibody isotypes across a wide range of species. The binding site comprises 4 amino acid residues with the first being either a Tyr or Phe and the remaining three Tyr, Tyr and Trp. While the binding pocket location and amino acid side-chain orientation are conserved in the crystal structure overlay, there are slight differences in the overall backbone sequence variation from antibody to antibody and in numbering schemes. This is demonstrated below by comparing the conserved nucleotide binding sites for the commercial antibodies Herceptin and Rituximab. Nucleotide mimetics (non-peptide, peptide, nucleotide analogue and amino acid) which have been rationally designed to interact with this domain via one or more of the amino acids described above are suitable affinity ligands for IgG binding and conjugation.

| Antibody | Amino Acid 1 | Amino Acid 2 | Amino Acid 3 | Amino Acid 4 |
|---|---|---|---|---|
| Herceptin | Light Chain Tyr 36 | Light Chain Tyr 87 | Heavy Chain Tyr 95 | Heavy Chain Trp 110 |
| Rituximab | Light Chain Phe 35 | Light Chain Tyr 86 | Heavy Chain Tyr 95 | Heavy Chain Trp 111 |

In an embodiment, the capture resin is able to bind to a conserved nucleotide domain in the Fab arm of an antibody.

A fourth defined region is the glycan structures present on Asn 297 in the CH2 domain of the Fc region of intact antibodies. m-Aminophenylboronic acid acting as an affinity ligand binds to cis diol groups on sugar residues such as mannose, galactose or glucose such that are present with the saccharide moiety of glycoprotein molecules. A reversible five membered ring complex is furnished from this interaction. A typical antibody glycan structure is shown in FIG. 6 to highlight the presence of mannose and galactose in antibody glycans (Adapted from Arnold et al, Advances in Experimental Medicine and Biology, 2005, 564, 27-43). In an embodiment, the capture resin is able to bind to a glycan structure present on Asn 297 in the CH2 domain of the Fc region of intact antibodies.

Ligands can be attached to a range of solid support matrices well known in the field of affinity chromatography. These include by example, synthetic polymers such as polyacrylamide, polyvinylalcohol or polystyrene, especially cross linked synthetic polymers, inorganic supports such as silica-based supports and in particular polysaccharide supports such as starch, cellulose and agarose.

Specific ligand-supports suitable for antibody binding are described below:

'Non Peptide' Protein A, G and L Mimetic Affinity Supports

Molecular modelling of the Protein A, G or L interaction combined with synthetic chemical library screening has enabled semi-rational design of small molecule mimetics of these proteins (Li et al, Nature Biotechnology, 1998, 16, 190-195). Examples of such resins include the commercially available supports mAbsorbent A1P and FAbsorbent F1P HF (ProMetic Biosciences).

mAbsorbent A1P and FAbsorbent F1P HF supports are formed on a triazine scaffold using a multicomponent Ugi reaction (www.prometicbioscience.com).

US20010045384 discloses a Protein A mimetic ligand-complex assembled upon an imino diacetate (IDA) type scaffold. The IDA scaffold is derivatised with triazyl ligands to afford a multivalent triazyl ligand-complex.

WO9808603 describes the isolation of immunoglobulins from cell culture supernatants, sera, plasma or colostrum using affinity resins. These affinity resins comprise of synthetic mono or bicyclic-aromatic or heteroaromatic ligands to facilitate immunoglobulin purification.

Another ligand with promise as an antibody affinity resin is sulfamethazine. Dextran microparticles coupled with sulfamethazine specifically bind antibodies (Yi et al, Prep. Biochem. Biotechnol., 2012, 42, 6, 598-610).

In the selection of the lead candidate ligands described above many ligands were excluded based on lack of antibody specificity. It is disclosed herein that specificity is less important than binding efficiency, capacity and stability for a solid phase antibody conjugation resin and as such these are not discounted.

'Peptide' Protein A, G or L Mimetic Affinity Supports

A number of Protein A mimetic peptides have been disclosed. Menegatti identified a hexapeptide with the sequence HWRGWV that binds to the antibody Fc region (Menegatti et al, Journal of Separation Science, 2012, 35, 22, 3139-3148. Fassina et al have identified a Protein A mimetic peptide TG191318 through synthesis and screening of synthetic multimeric peptide libraries composed of randomized synthetic molecules with a tetradendate lysine core (Fassina et al, J. Mol. Recognit., 1996, 9, 564). EP1997826 discloses a peptide comprising $X_1$-Arg-Thr-Tyr. Lund et al discloses two peptide ligands suitable for antibody affinity chromatography (Lund et al, J Chromatogr. A, 2012, 1225, 158-167). DAAG and $D_2$AAG contain L-arginine, L-glycine and a synthetic aromatic acid 2,6-di-tert-butyl-4-hydroxybenzyl acrylate (DBHBA)

Amino Acid Protein A, G or L Mimetic Affinity Supports

In addition to the complex macromolecular ligands described above simple amino acids have been proposed as Protein A mimetics that bind antibodies in the same way (Naik et al, J. Chromatogr. A, 2011, 1218, 1756-1766). An example of this is AbSep a tryptophan containing polymethacrylate resin with a high affinity for the Protein A binding site in the Fc region of antibodies. Resins containing the amino acids Tyrosine, Histidine and Phenylalanine are also suitable for antibody immobilisation and conjugation (Bueno et al, J. Chromatogr. B, Biomed. Appl., 1995; 667, 1, 57-67).

Nucleotide Binding Site Affinity Supports

Another strategy for developing antibody purification ligands has exploited the lesser known conserved nucleotide binding site (NBS) in the Fab variable regions of antibodies (Alves et al, Anal. Chem., 2012, 84, 7721-7728). The nucleotide analogue indolebutyric acid has been coupled to a ToyoPearl AF-650-amino M resin to prepare a support which meets criterion 1-5 above. An extensive range of other nucleotide analogues useful for antibody affinity chromatography is described in WO/2012/099949.

Carbohydrate Binding Resins

The ligand m-aminophenylboronic acid immobilised on a variety of supports has been used to purify glycoproteins. The ligand binds to cis-diol groups on sugar residues such as mannose, galactose, or glucose that are present within the saccharide moiety of glycoprotein molecules including antibodies, forming a reversible five-member ring complex. This complex can be dissociated by lowering the pH, or by using an elution buffer containing either Tris or sorbitol.

A ligand of the capture resin is able to interact with a biomolecule by specific, reversible and non-covalent bond interactions between the ligand and the biomolecule, e.g. a protein, antibody, modified antibody or antibody fragment. Non-covalent interactions may be classified as ionic, van der Waals, hydrogen bond or hydrophobic. These interactions work in a 3-dimensional manner to assist in the flexibility and conformation of the target biomolecule to the ligand of the capture resin. When in close proximity to the ligand, the biomolecule may infer one, several or all of these interactions to afford a ligand-biomolecule complex. The distance between the ligand and the biomolecule and the polarity and electronegativity of the ligand will determine the intensity of these interactions. Furthermore, the intensity of these interactions may be defined as the affinity force. A high affinity force between a ligand and a biomolecule constitutes a ligand-biomolecule complex of enhanced stability (US2009/0240033).

In an embodiment the capture resin comprises a non-peptide-based Protein A, Protein G or Protein L mimetic. The capture resin is able to bind an antibody, modified antibody or antibody fragment.

Non-peptide-based Protein A, Protein G or Protein L mimetics have been used in dye ligand chromatography, which is a mode of affinity chromatography that utilizes covalently bond textile dyes immobilised to a solid support such as agarose to purify proteins. These dyes resemble natural substrates/protein ligands to which proteins have affinities for. This mode of purification and separation is often referred to as pseudo-affinity chromatography. Dye ligand affinity chromatography is non-specific but the technique is advantageous for a broad binding range for a variety of proteins. Advances in the purification technique employed modified dyes to act as competitive inhibitors for a proteins normal substrate/ligand (P. Dean et al, J. Chromatography, 1979, 165, 3, 301-319). Triazinyl based ligands such as Cibacron Blue 3GA, Procion Red H-3B, Procion Blue MX 3G, Procion Yellow H-A, etc. are commonly employed and address the concerns of purity, leakage and toxicity of the original commercial dyes such as Blue Dextran (Lowe et al, Trends Biotechnology, 1992, 10, 442-448). Triazinyl ligands have been successfully used for the purification of albumin, oxidoreductases, decarboxylases, glycolytic enzymes, nucleases, hydroloases, lyases, synthetases and transferases (N. Labrou, Methods Mol. Biol. 2002, 147, 129-139). A limitation of biomimetic dye ligand affinity chromatography is that the affinity strength from biomolecule to biomolecule is considerably variable and in many cases a ligand that affords strong affinity strength for a protein may not be applicable to another protein. Therefore, it is often a necessity that an extensive and empirical screening process is undertaken to identify suitable synthetic ligands with desired affinity for a biomolecule of interest.

Consequently to assist in the structured elucidation of suitable ligands that effect affinity binding to a biomolecule a multivalent scaffold motif has been incorporated into the ligand structure to provide a construct to which a library of ligands may be introduced and screened in combination with rigid spatial separation of the ligand from the support.

In an embodiment, the ligand of the capture resin has a structure according to the structures recited in the disclosure of WO98/08603. The capture resins of WO98/08603 comprise synthetic mono or bicyclic-aromatic or heteroaromatic ligands to facilitate immunoglobulin purification. The contents of WO98/08603 relating to the structure of the capture resin are incorporated herein by reference. WO98/08603 describes the isolation of immunoglobulins from cell culture supernatants, sera, plasma or colostrum using affinity resins.

In an embodiment, the ligand of the capture resin has a structure according to the structures recited in the disclosure of WO2009/141384. The capture resins of WO2009/141384 have the general formula:

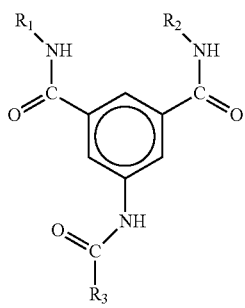

wherein $R_1$, $R_2$ and $R_3$ represent organic moieties of a molecular weight of 15-1000 g/mol, the total weight being 200-2000 g/mol, to which the ligand is immobilised to a solid phase support through an amide bond through one of $R_1$, $R_2$ and $R_3$. The contents of WO2009/141384 relating to the structure of the capture resin are incorporated herein by reference. WO2009/141384 describes that the ligands bind proteinaceous Factor VII polypeptides.

In an embodiment, the ligand of the capture resin has a structure according to the structures recited in the disclosure of US20010045384. The capture resins of US20010045384 are Protein A mimetic ligand-complexes assembled upon an imino diacetate (IDA) type scaffold. The contents of US20010045384 relating to the structure of the capture resin are incorporated herein by reference. The IDA scaffold is derivatatised with triazyl ligands to afford a multivalent triazyl ligand-complex. An illustrative triazyl ligand complex defined within US20010045384 is shown below:

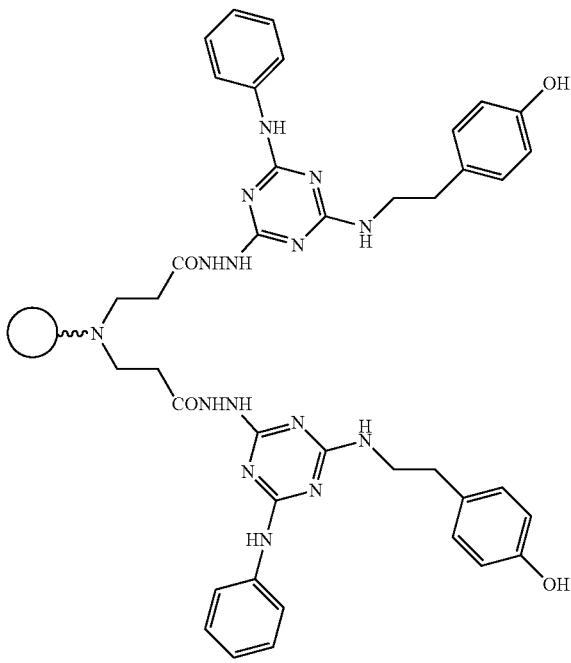

This Protein A mimetic has been demonstrated for utility as an affinity purification media for immunoglobulins such as IgG. It is postulated that the molecular geometry of the adjacent triazine ligands in the ligand-complex is an advantage using the IDA scaffold.

Another illustrative complex defined within US20010045384 is shown below:

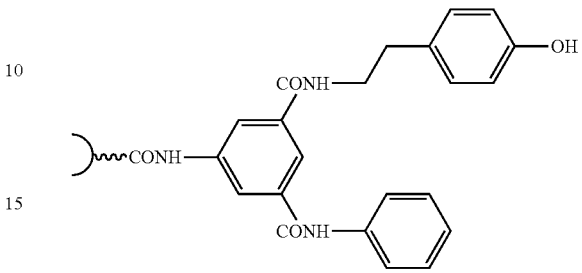

This branched multivalent phthalic acid-ligand scaffold Protein A mimetic ligand-complex was demonstrated to have affinity for immunoglobulins.

In an embodiment, the ligand of the capture resin has a structure according to the structures recited in the disclosure of WO9710887 and U.S. Pat. No. 6,117,996. The contents of WO9710887 and U.S. Pat. No. 6,117,996 relating to the structure of the capture resin are incorporated herein by reference. WO9710887 and U.S. Pat. No. 6,117,996 disclose a triazyl-ligand affinity construct of the type:

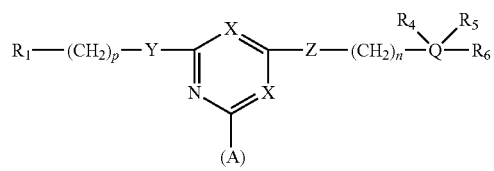

wherein, (A) represents the covalent attachment point of the triazine scaffold to a polysaccharide solid support optionally through a spacer arm interposed between the ligand and the solid support, and $R_1$ and Q are optionally substituted ligands with affinity for proteinaceous materials. The organic moieties are described as Protein A mimetics and are proposed and exemplified as alternative purification media to Protein A for the purification of proteinaceous materials.

In an embodiment, the ligand of the capture resin has a structure according to the structures recited in the disclosure of WO2004/035199. The content of WO2004/035199 relating to the structure of the capture resin is incorporated herein by reference. WO2004/035199 discloses the use of a Protein L mimetic comprising of a branched ligand scaffold of general formula,

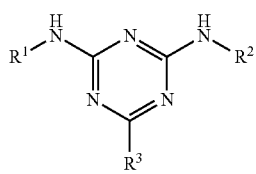

wherein $R^1$ and $R^2$ are the same or different and are each optionally substituted alkyl or aryl ligands, and $R^3$ is a solid support optionally attached by a spacer motif. The triazyl-ligand scaffold has been disclosed as suitable Protein L mimetic ligands for the affinity binding of immunoglobulin or fragment antibodies (fAb) thereof. Furthermore, it is disclosed that these triazyl-ligand scaffolds have preferential binding affinity for immunoglobulin K and λ light chains.

In an embodiment, the ligand of the capture resin has a structure according to the structures recited in the disclosure of US20110046353. The content of US20110046353 relating to the structure of the capture resin is incorporated herein by reference. US20110046353 discloses the purification of a fragment antibody (fAb) from a production medium. Fragment antibodies cannot be purified on Protein A media. The fAb is characterised as having a binding domain capable of binding to an antigen and in many embodiments disclosed within consists of having one heavy chain (Vh), or a functional fragment thereof, and one light chain (Vl), or a functional fragment thereof, together with at least one other chain. Defined within are affinity ligands for fAb, consisting of a branched triazyl scaffold of the formula,

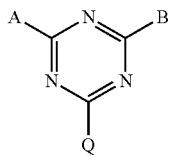

wherein Q represents the attachment point to a solid support matrix, optionally with a spacer motif and Groups A and B are phenyl or naphthyl groups substituted with one or more substituents capable of hydrogen bonding, preferably one or more of —OH, —SH or —CO₂H. Excellent results have been reported using supported affinity ligands commercially available from Prometic Biosciences under the trade names MAbsorbent A1P and MAbsorbent A2P.

In an embodiment, the ligand of the capture resin has a structure:

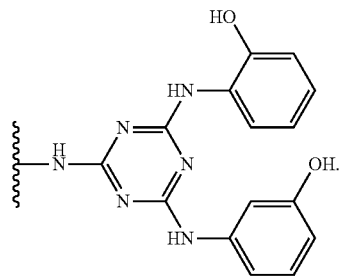 [SMILES: *Nc1nc(Nc2cccc(O)c2)nc(Nc2ccccc2O)n1]

In an embodiment, the ligand of the capture resin has a structure:

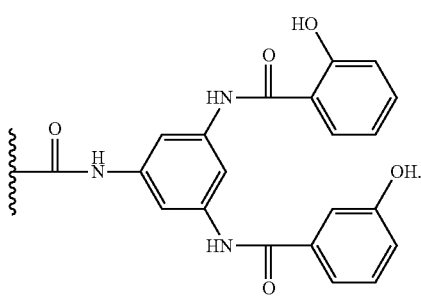 [SMILES: *C(=O)Nc1cc(NC(=O)c2cccc(O)c2)cc(NC(=O)c2ccccc2O)c1]

In an embodiment, the ligand of the capture resin has a structure:

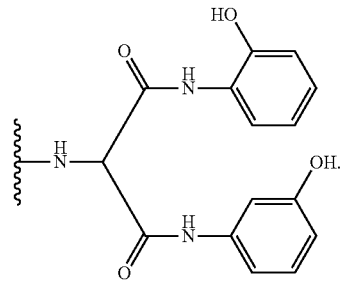 [SMILES: *NC(C(=O)Nc1cccc(O)c1)C(=O)Nc1ccccc1O]

In an embodiment, the capture resin is in the form of a bead. In an embodiment, the size of the bead in terms of the bead diameter is from about 10 μm to about 2000 μm, preferably from about 50 μm to about 1000 μm, and most preferably from about 75 μm to about 500 μm.

In an embodiment, the capture resin includes a mobile support made from a material selected from the group consisting of: Polystyrene, Polystyrene (PS-DVB)—Lightly cross-linked with divinylbenzene (0.1-5.0% DVB, termed Microporous), Polystyrene (PS-DVB)—Highly cross-linked with divinylbenzene (5-60% DVB, termed Macroporous), Polyethylene glycol, Polyethylene glycol grafted polystyrene (PS-PEG co-polymer), Poly acrylamide, Controlled Pore Glass (CPG) beads, Silica, Kieselguhr, Polypropylene, Poly(tetrafluoroethylene), Polyethylene, Cellulose, Poly methacrylate, Functionalised Monoliths, Functionalised Fibres, Monolithic columns (such as Nikzad et al, OPRD, 2007, 11, 458-462), Agarose, Sepharose and Magnetic recoverable polymer beads.

In a preferred embodiment, the capture resin is a mobile support made from a material selected from the group consisting of: Agarose, Sepharose and Cellulose.

In an embodiment, the capture resin is a commercially available capture resin such as Fabsorbant™ F1P HF resin. In an embodiment, the capture resin is a commercially available capture resin such as Mabsorbant™ resin.

Biomolecule:

In an embodiment, the biomolecule naturally occurs in a living organism. Alternatively, the biomolecule may be a derivative of a chemical compound that naturally occurs in a living organism. For example, the biomolecule may be biomolecule that has been altered chemically or genetically in a way which does not affects its biological activity.

In an embodiment, the biomolecule is an antibody.

In an embodiment, the biomolecule is a modified antibody, e.g. an antibody including a non-natural amino acid.

In an embodiment, the biomolecule is an antibody fragment.

In an embodiment, the antibody is a monoclonal antibody.

In an embodiment, the antibody is trastuzumab.

In an embodiment, the antibody, modified antibody or antibody fragment is an immunoglobulin (Ig), e.g. one of the five human immunoglobulin classes: IgG, IgA, IgM, IgD and IgE. The term antibody encompasses monoclonal antibodies. The term antibody encompasses polyclonal antibodies. The term antibody encompasses antibody fragments so long as they exhibit the desired biological activity. The antibody can be a human antibody, an animal antibody, a murine antibody, a humanised antibody or a chimeric antibody that comprises human and animal sequences.

The basic unit of the antibody structure is a heterotetrameric glycoprotein complex of at least 20,000 Daltons, for example about 150,000 Daltons. An antibody might be at least 900 amino acids in length, for example 1400 amino acids in length. An antibody may composed of two identical light (L) chains and two identical heavy (H) chains, linked together by both non-covalent associations and by di-sulfide bonds. Each heavy and light chain also has regularly spaced intrachain disulfide bridges. Each heavy chain is about 50,000 Daltons. Each heavy chain is at least 300 amino acids in length, for example about 450 amino acids in length. The antibody may be a heavy chain only antibody. Each light chain is about 20,000 Daltons. Each light chain is at least 100 amino acids in length, for example about 250 amino acids in length.

An antibody biomolecule can contain two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell).

In an embodiment the biomolecule is an antibody fragment. Antibody fragments comprise a portion of a full length antibody, generally the antigen binding or variable region thereof.

Examples of antibody fragments include Fab, pFc', F(ab')2, and scFv fragments; diabodies; linear antibodies; single-chain antibody biomolecules; and multispecific antibodies formed from antibody fragments. An antibody fragment might be at least 10 amino acids in length, for example an antibody fragment might be at least 20, 40, 60, 80, 100, 120, 140, 160, 180, 200, 220, 240, 260, 280 or 300 amino acids in length.

In an embodiment the biomolecule is a modified antibody or a modified antibody fragment. By "modified antibody" or "modified antibody fragment" is meant an antibody that differs from a parent antibody by virtue of at least one amino acid modification. A modified antibody or modified antibody fragment refers to an antibody, which in comparison to the wild-type antibody, is different with respect to its size, or which is different with respect to its glycosylation but which has a similar affinity to its ligand as the wild-type antibody.

Drug:

The term "drug" includes any substance that, when administered into the body of a living organism, alters normal bodily function. Generally a drug is a substance used in the treatment, cure, prevention, or diagnosis of disease or used to otherwise enhance physical or mental well-being. In an embodiment, the drug is a cytotoxic drug.

The leading 'ultra-potency' (drug) candidates to date are defined in one of two categories: (i) tubulin inhibitors; and (ii) DNA interacting agents. Tubulin inhibitors modulate tubulin polymerization. DNA interacting agents target cellular DNA In an embodiment the drug is a tubulin inhibitor.

In an embodiment, the tubulin inhibitor is selected from the group consisting of: (a) an auristatin; and (b) a maytansine derivative.

In an embodiment, the drug is an auristatin.

Auristatins include synthetic derivatives of the naturally occurring compound Dolastatin-10. Auristatins are a family of antineoplastic/cytostatic pseudopeptides. Dolastatins are structurally unique due to the incorporation of 4 unusual amino acids (Dolavaine, Dolaisoleuine, Dolaproine and Dolaphenine) identified in the natural biosynthetic product. In addition this class of natural product has numerous asymmetric centres defined by total synthesis studies by Pettit et al (U.S. Pat. No. 4,978,744). It would appear from structure activity relationships that the Dolaisoleuine and Dolaproine residues appear necessary for antineoplastic activity (U.S. Pat. No. 5,635,483 and U.S. Pat. No. 5,780,588).

In an embodiment, the auristatin is selected from the group consisting of: Auristatin E (AE); Monomethylauristatin E (MMAE); Auristatin F (MMAF); vcMMAE; and vcMMAF.

In an embodiment, the drug is a maytansine or a structural analogue of maytansine.

In an embodiment, the drug is a maytansine.

Maytansines include structurally complex antimitotic polyketides. Maytansines are potent inhibitors of microtubulin assembly which leads towards apoptosis of tumour cells.

In an embodiment the maytansine is selected from the group consisting of: Mertansine (DM1); and a structural analogue of maytansine such as DM3 or DM4. Preferably, the drug is mertansine (DM1).

In an embodiment, the drug is DNA interacting agent. DNA interacting agents are known as 'ultra-potent' (drug) candidates.

In an embodiment, the DNA interacting agent is selected from the group consisting of: (a) calicheamicins, (b) duocarmycins and (c) pyrrolobenzodiazepines (PBDs).

In an embodiment, the drug is a calicheamicin.

Calicheamicin is a potent cytotoxic agent that causes double-strand DNA breaks, resulting in cell death. Calicheamicin is a naturally occurring enediyne antibiotic (A. L. Smith et al, J. Med. Chem., 1996, 39, 11, 2103-2117). Calicheamicin was found in the soil microorganism *Micromonosporaechinospora*.

In an embodiment, the calicheamicin is calicheamicin gamma 1.

In an embodiment, the drug is a duocarmycin.

Duocarmycins are potent anti-tumour antibiotics that exert their biological effects through binding sequence-selectively in the minor groove of DNA duplex and alkylating the N3 of adenine (D. Boger, Pure & Appl. Chem., 1994, 66, 4, 837-844).

In an embodiment, the duocarmycin is selected from the group consisting of: Duocarmycin A; Duocarmycin B1; Duocarmycin B2; Duocarmycin C1; Duocarmycin C2; Duocarmycin D; Duocarmycin SA; Cyclopropylbenzoindole (CBI) duocarmycin; Centanamycin; Rachelmycin (CC-1065); Adozelesin; Bizelesin; and Carzelesin.

In an embodiment, the drug is a pyrrolobenzodiazepine.

Pyrrolobenzodiazepines (PBDs) are a class of naturally occurring anti-tumour antibiotics. Pyrrolobenzodiazepines are found in *Streptomyces*. PBDs exert their anti-tumour activity by covalently binding to the DNA in the minor groove specifically at purine-guanine-purine units. They insert on to the N2 of guamine via an aminal linkage and, due to their shape, they cause minimal disruption to the DNA helix. It is believed that the formation of the DNA-PBD adduct inhibits nucleic acid synthesis and causes excision-dependent single and double stranded breaks in the DNA helix. As synthetic derivatives the joining of two PBD units together via a flexible polymethylene tether allows the PBD dimers to cross-link opposing DNA strands producing highly lethal lesions.

In an embodiment, the drug is a synthetic derivative of two pyrrolobenzodiazepines units joined together via a flexible polymethylene tether.

In an embodiment, the pyrrolobenzodiazepine is selected from the group consisting of: Anthramycin (and dimers thereof); Mazethramycin (and dimers thereof); Tomaymycin (and dimers thereof); Prothracarcin (and dimers thereof); Chicamycin (and dimers thereof); Neothramycin A (and dimers thereof); Neothramycin B (and dimers thereof); DC-81 (and dimers thereof); Sibiromycin (and dimers thereof); Porothramycin A (and dimers thereof); Porothramycin B (and dimers thereof); Sibanomycin (and dimers thereof); Abbeymycin (and dimers thereof); SG2000; and SG2285.

In an embodiment, the drug is a drug that targets DNA interstrand crosslinks through alkylation. A drug that targets DNA interstrand crosslinks through alkylation is selected from: a DNA targeted mustard; a guanine-specific alkylating agent; and a adenine-specific alkylating agent.

In an embodiment, the drug is a DNA targeted mustard. For example, the DNA targeted mustard may be selected from the group consisting of: an oligopyrrole; an oligoimidazole; a Bis-(benzimidazole) carrier; a Polybenzamide Carrier; and a 9-Anilinoacridine-4-carboxamide carrier.

In an embodiment, the drug is selected from the group consisting of: Netropsin; Distamycin; Lexitropsin; Tallimustine; Dibromotallimustine; PNU 157977; and MEN 10710.

In an embodiment, the drug is a Bis-(benzimidazole) carrier. Preferably, the drug is Hoechst 33258.

A guanine-specific alkylating agent is a highly regiospecific alkylating agents that reacts at specific nucleoside positions.

In an embodiment, the drug is a guanine-specific alkylating agent selected from the group consisting of: a G-N2 alkylators; a A-N3 alkylator; a mitomycin; a carmethizole analogue; a ecteinascidin analogue.

In an embodiment, the mitomycin is selected from: Mitomycin A; Mitomycin C; Porfiromycin; and KW-2149.

In an embodiment, the a carmethizole analogue is selected from: Bis-(Hydroxymethyl)pyrrolizidine; and NSC 602668.

In an embodiment, the ecteinascidin analogue is Ecteinascidin 743.

Adenine-specific alkylating agents are regiospecific and sequence-specific minor groove alkylators reacting at the N3 of adenines in polypyrimidines sequences. Cyclopropaindolones and duocamycins may be defined as adenine-specific alkylators.

In an embodiment, the drug is a cyclopropaindolone analogue. Preferably, the drug is selceted from: adozelesin; and carzelesin.

In an embodiment, the drug is a benz[e]indolone. Preferably, the drug is selected from: CBI-TMI; and iso-CBI.

In an embodiment, the drug is bizelesin.

In an embodiment, the drug is a Marine Antitumor Drug. Marine Antitumor Drugs has been a developing field in the antitumor drug development arena (I. Bhatnagar et al, Mar. Drugs 2010, 8, P2702-2720 and T. L. Simmons et al, Mol. Cancer Ther. 2005, 4(2), P333-342). Marine organisms including sponges, sponge-microbe symbiotic association, gorgonian, actinomycetes, and soft coral have been widely explored for potential anticancer agents.

In an embodiment, the drug is selected from: Cytarabine, Ara-C; Trabectedin (ET-743); and EribulinMesylate.

In an embodiment, the EribulinMesylate is selected from: (E7389); Soblidotin (TZT 1027); Squalamine lactate; CemadotinPlinabulin (NPI-2358); Plitidepsin; Elisidepsin; Zalypsis; Tasidotin, Synthadotin; (ILX-651); Discodermolide; HTl286; LAF389; Kahalalide F; KRN7000; Bryostatin 1; Hemiasterlin (E7974); Marizomib; Salinosporamide A; NPI-0052); LY355703; CRYPTO 52; Depsipeptide (NSC630176); Ecteinascidin 743; Synthadotin; Kahalalide F; Squalamine; Dehydrodidemnin B; Didemnin B; Cemadotin; Soblidotin; E7389; NVP-LAQ824; Discodermolide; HTI-286; LAF-389; KRN-7000 (Agelasphin derivative); Curacin A; DMMC; Salinosporamide A; Laulimalide; Vitilevuamide; Diazonamide; Eleutherobin; Sarcodictyin; Peloruside A; Salicylihalimides A and B; Thiocoraline; Ascididemin; Variolins; Lamellarin D; Dictyodendrins; ES-285 (Spisulosine); and Halichondrin B.

The following drugs are also encompassed by the present invention: Amatoxins (α-amanitin)-bicyclic octapeptides produced by basidiomycetes of the genus *Amanita*, e.g. the Green Deathcap mushroom; Tubulysins; Cytolysins; dolabellanins; Epothilone A, B, C, D, E, F.

Epothilones—constitute a class of non-taxane tubulin polymerisation agents and are obtained by natural fermentation of the myxobacterium *Sorangium cellulosum*. These moieties possess potent cytotoxic activity which is linked to the stabilisation of microtubules and results in mitotic arrest at the G2/M transition. Epothilones have demonstrated potent cytotoxicity across a panel of cancer cell lines and has often exhibited greater potency than paclitaxel (X.: Pivot et al, European Oncology, 2008; 4(2), P42-45).

In an embodiment, the drug is amatoxin.
In an embodiment, the drug is tubulysin.
In an embodiment, the drug is cytolysin.
In an embodiment, the drug is dolabellanin.
In an embodiment, the drug is epothilone.

The following drugs are also encompassed by the present invention. In an embodiment, the drug is selected from: Doxorubicin; Epirubicin; Esorubicin; Detorubicin; Morpholino-doxorubicin; Methotrexate; Methopterin; Bleomycin; Dichloromethotrexate; 5-Fluorouracil; Cytosine-β-D-arabinofuranoside; Taxol; Anguidine; Melphalan; Vinblastine; Phomopsin A; Ribosome-inactivating proteins (RIPs); Daunorubicin; *Vinca* alkaloids; Idarubicin; Melphalan; Cis-platin; Ricin; Saporin; Anthracyclines; Indolinobenzodiazepines; 6-Mercaptopurine; Actinomycin; Leurosine; Leurosideine; Carminomycin; Aminopterin; Tallysomycin; Podophyllotoxin; Etoposide; Hairpin polyamides; Etoposide phosphate; Vinblastine; Vincristine; Vindesine; Taxotere retinoic acid; N8-acetyl spermidine; Camptothecin; Esperamicin; and Ene-diynes.

In an embodiment, the drug is Doxorubicin.
In an embodiment, the drug is Epirubicin.
In an embodiment, the drug is Esorubicin.
In an embodiment, the drug is Detorubicin.
In an embodiment, the drug is Morpholino-doxorubicin.
In an embodiment, the drug is Methotrexate.
In an embodiment, the drug is Methopterin.
In an embodiment, the drug is Bleomycin.
In an embodiment, the drug is Dichloromethotrexate.
In an embodiment, the drug is 5-Fluorouracil.
In an embodiment, the drug is Cytosine-β-D-arabinofuranoside.
In an embodiment, the drug is Taxol.
In an embodiment, the drug is Anguidine.
In an embodiment, the drug is Melphalan.
In an embodiment, the drug is Vinblastine.
In an embodiment, the drug is Phomopsin A.
In an embodiment, the drug is Ribosome-inactivating proteins (RIPS).
In an embodiment, the drug is Daunorubicin.

In an embodiment, the drug is *Vinca* alkaloids.
In an embodiment, the drug is Idarubicin.
In an embodiment, the drug is Melphalan.
In an embodiment, the drug is Cis-platin.
In an embodiment, the drug is Ricin.
In an embodiment, the drug is Saporin.
In an embodiment, the drug is Anthracyclines.
In an embodiment, the drug is Indolino-benzodiazepines.
In an embodiment, the drug is 6-Mercaptopurine.
In an embodiment, the drug is Actinomycin.
In an embodiment, the drug is Leurosine.
In an embodiment, the drug is Leurosideine.
In an embodiment, the drug is Carminomycin.
In an embodiment, the drug is Aminopterin.
In an embodiment, the drug is Tallysomycin.
In an embodiment, the drug is Podophyllotoxin.
In an embodiment, the drug is Etoposide.
In an embodiment, the drug is Hairpin polyamide.
In an embodiment, the drug is Etoposide phosphate.
In an embodiment, the drug is Vinblastine.
In an embodiment, the drug is Vincristine.
In an embodiment, the drug is Vindesine.
In an embodiment, the drug is Taxotere retinoic acid.
In an embodiment, the drug is N8-acetyl spermidine.
In an embodiment, the drug is Camptothecin.
In an embodiment, the drug is Esperamicin.
In an embodiment, the drug is Ene-diyne.
Biomolecule-Drug-Conjugates:
In accordance with the present invention there is provided a biomolecule-drug-conjugate obtainable by a process of the present invention.

BRIEF DESCRIPTION OF THE DRAWINGS

Embodiments of the invention are further described hereinafter with reference to the accompanying drawings, in which.

DETAILED DESCRIPTION

Figure 1:
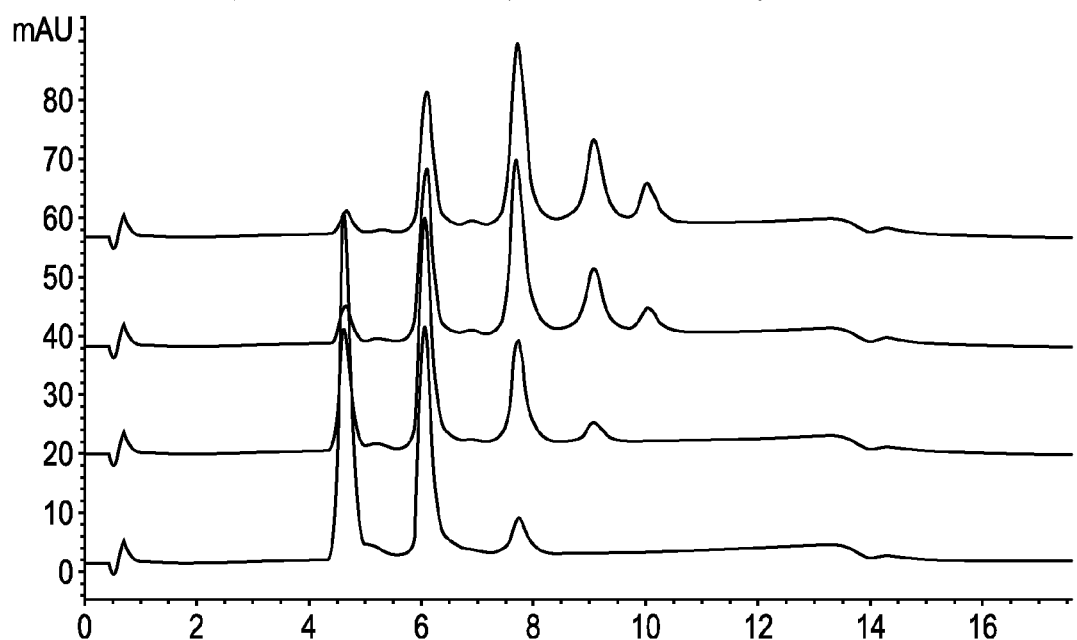
FIG. 1—HIC Analysis of Solid Phase Herceptin vcMMAE Conjugates produced by Example 2. Traces from bottom to top Herceptin-vcE$_{1.3}$, Herceptin-vcE$_{2.4}$, Herceptin-vcE$_{3.4}$, Herceptin-vcE$_{4.4}$. RT 4.3 min—Unconjugated Herceptin, RT 5.9 min—Drug antibody ratio of 2, RT 7.5 min—Drug antibody ratio of 4, RT 8.9 min—Drug antibody ratio of 6 and RT 9.8 min—Drug antibody ratio of 8.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

The following techniques are used in the examples.
Size Exclusion Chromatography (SEC)
Size exclusion chromatography was performed using a TOSOH Bioscience TSK-Gel® GW3000SWxl column in 0.2M potassium phosphate pH 6.95 with 0.25 mM potassium chloride and 10% IPA at a flow rate of 0.5 ml/min. Aggregation state of the conjugate was determined by integration of eluted peak area absorbance at 280 nm.

Hydrophobic Interaction Chromatography (HIC)
Hydrophobic interaction chromatography was performed using a TOSOH TSK-Gel® butyl NPR column with a linear gradient of 0-100% buffer A to B over 12 minutes at a flow rate of 0.8 ml/min. Where buffer A is 1.5 M ammonium acetate pH 6.95 with 25 mM sodium phosphate and buffer B is 25 mM sodium phosphate pH 6.95 with 25% IPA. Antibody drug ratio of the conjugate was determined by integration of eluted peak area absorbance at 280 nm.

Reverse Phase Chromatography (RP-PLRP)
Reverse phase (polymer labs PLRP) chromatography was performed using an Agilent PLRP-S PL1912-1502 column with a gradient of 25-95% buffer A to B over 31 minutes at a flow rate of 0.25 ml/min. Where buffer A is Water with 0.05% TFA and buffer B is ACN with 0.04% TFA. Samples were reduced pre injection with 20 mM sodium borate pH 8.4 p containing 50 mM DTT at 37° C. for 15 minutes.

Antibody drug ratio of the conjugate was determined by integration of eluted peak area absorbance at 280 nm.

Drug to Antibody Ratio by UV Analysis

For UV analysis the sample was added to a 400 ul quartz cuvette with a path length of 1 cm and the absorbance at 252 nm and 280 nm measured on a Thermo scientific multiskan GO spectrophotometer. The 252 nm and 280 nm data was used to calculate Drug antibody ratio based on published molar extinction coefficients for Herceptin and DM1 at these wavelengths.

Example 1—Solid Phase Antibody Drug Conjugate Screening

This example demonstrates that immobilized antibodies can be conjugated to a defined drug loading with a generic process that negates the need for process development. This approach is suitable for adapting to 96 well plate high throughput screening.

Herceptin (0.5 of 1 mg/ml in PBS, pH 7.4) was bound to 100 µl (settled resin volume) of Fabsorbant™ F1P HF resin equilibrated in PBS by mixing the resin slurry and antibody solution gently for 60 minutes. Unbound Herceptin was removed by washing the resin with PBS, 2 mM EDTA and the resin finally re-suspended in 0.5 ml PBS/EDTA.

The bound Herceptin (Her) was reduced by adding tris-(2-carboxyethyl)phosphine hydrochloride to a final concentration of 2 mM and then incubating the suspension at ambient temperature for 18 hours. The resin was washed with PBS/EDTA to remove unreacted TCEP and then re-suspended in 475 µl PBS/EDTA.

vcMMAE (vcE), N-ethyl maleimide (NEM) and dimethylacetamide (DMA) were added to achieve final concentrations of 1 mM maleimide (total vcE and NEM) and 5% v/v DMA. The ratio of vcE to NEM was varied 100:0, 75:25, 50:50, 25:75 and 0:100. The reduced antibody was conjugated by incubating the resin suspension at ambient for 60 minutes. The resin was washed sequentially with PBS/EDTA/5% v/v DMA and 0.1M Glycine pH 5.0.

The conjugates were eluted with 0.1M glycine pH3.0. The eluted conjugates were collected into 2% v/v of 1M tris(hydroxymethyl)aminoethane (TRIS) to neutralise them.

The neutralised conjugates were then analysed by Size Exclusion Chromatography and Reverse Phase Chromatography (Polymer Labs, PLRP) Chromatography to determine the percentage aggregate and average drug loading.

The results are summarized in Table 1 below:

| Mass of Her Bound (mg/ml resin) | Ratio of vcE:NEM | % Aggregate | Drug to Antibody ratio (DAR) |
|---|---|---|---|
| 10 | 100:0 | 9.72 | 7.9 |
| 10 | 75:25 | 4.69 | 5.7 |
| 10 | 50:50 | 3.08 | 4.4 |
| 10 | 25:75 | 0.80 | 2.8 |
| 10 | 0:100 | 0.42 | 0.0 |

The aggregate content of even the highest drug loaded conjugates is acceptable for further evaluation in antigen binding and cell based assays. The sequential washes with PBS/ETDA/5% v/v DMA and then 0.1M glycine pH5.0 ensure the final conjugates are free from unreacted drug linker, NEM and solvent and do not compromise interpretation of bioassay data. With Fabsorbant™ F1P HF resin this approach is useful for screening panels of murine monoclonals as part of clone selection for subsequent antibody drug conjugation development, for producing ADCs direct from tissue culture supernatants containing both intact and Fab fragment antibodies.

Example 2—Solid Phase Partial TCEP Reduction in Batch Mode

This example shows that immobilized antibodies can be conjugated to a defined drug loading by partial reduction of the interchain disulphide bonds followed by conjugation with vcMMAE and that product quality is enhanced relative to the same conjugates made in solution.

Herceptin (0.5 ml of 2 mg/ml PBS, pH 7.4) was bound to 100 µl (settled resin volume) of Fabsorbant™ F1P HF resin equilibrated in PBS by mixing the resin slurry and antibody solution gently for 30 minutes. Unbound Herceptin was removed by washing the resin with PBS, 2 mM EDTA and the resin finally re-suspended in 0.5 ml PBS/EDTA.

The bound Herceptin was reduced by adding tris-(2-carboxyethyl)phosphine hydrochloride to a ratio of 1 to 4 moles of TCEP per mole of Herceptin and then incubating the suspension at ambient temperature for 2 hours.

vcMMAE and Dimethylacetamide (DMA) were added to achieve 2.5 to 10 moles of vcMMAE per mole of Herceptin and 5% v/v DMA and the conjugation allowed to proceed for 30 minutes at ambient. N-Acetyl cysteine (NAC) was added to quench unreacted vcMMAE and allowed to react for 20 minutes before the resin was washed sequentially with PBS/EDTA/5% v/v DMA and 0.1M glycine pH5.0.

The conjugates eluted with 0.1M glycine pH3.0. The eluted conjugates were collected into 2% v/v of 1M tris(hydroxymethyl)aminoethane (TRIS) to neutralise them.

An equivalent series of solution phase conjugates of Herceptin with vcMMAE with matched DAR were produced and analysed to provide a comparison of solid phase and solution phase conjugate quality.

Figure 2:
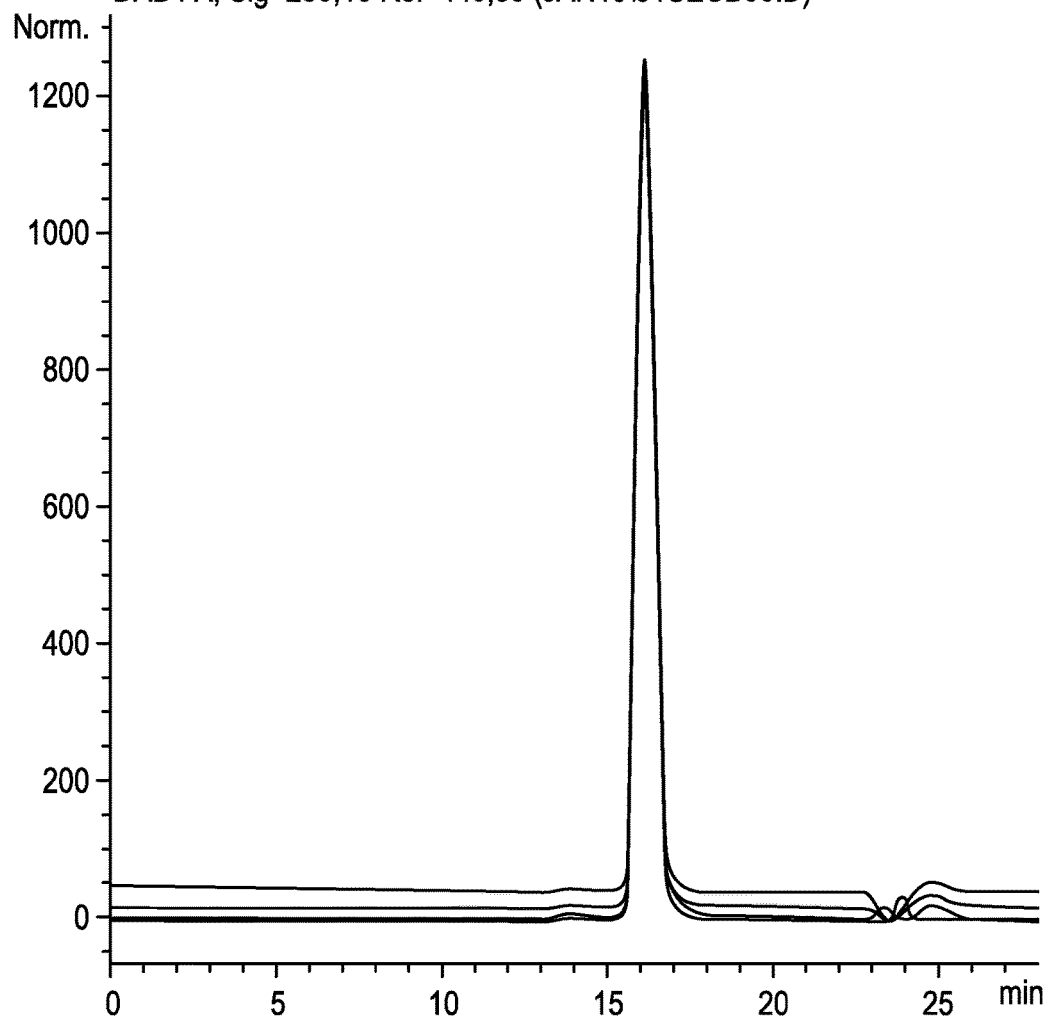
FIG. 2—SEC Analysis of Solid Phase Herceptin vcMMAE Conjugates produced by Example 2. Traces from bottom to top Herceptin, Herceptin-vcE$_{1.3}$, Herceptin-vcE$_{2.4}$, Herceptin-vcE$_{3.4}$, Herceptin-vcE$_{4.4}$.

The eluted conjugates were then analysed by Hydrophobic Interaction Chromatography (FIG. 1) and Size Exclusion Chromatography (FIG. 2) to determine the percentage aggregate and average drug loading.

The results are summarized in Table 2 below:

| DAR | Solution % Aggregate | Solid % Aggregate |
|---|---|---|
| 0 (Herceptin) |  | 0.2 |
| 1.3 | 0.4 | 0.3 |
| 2.4 | 0.7 | 0.3 |
| 3.4 | 1.1 | 0.3 |
| 4.4 | 1.5 | 0.3 |

The data show that on solid supports the relationship between TCEP to antibody ratio and final drug loading is linear. In addition when compared with an equivalent conjugate made in solution the solid phase conjugates show a lower percentage aggregation.

Example 3—Solid Phase Partial TCEP Reduction on Column

This example shows that immobilized antibody conjugation can be adapted to a chromatographic flow process with excellent reproducibility.

Herceptin (5 ml of 2 mg/ml PBS, pH 7.4) was bound to a 1 ml column of Fabsorbant™ F1P HF resin (previously equilibrated in PBS) by loading at 120 cm/hr. The bound Herceptin was prepared for reduction by equilibrating the resin with PBS, 2 mM EDTA.

A micro peristaltic pump was used to create a small volume PBS/EDTA recirculation loop through the column (approximately 200 μL external to the column) to which TCEP was added to give a molar ratio of 2 TCEP per mole of Herceptin. This was allowed to recirculate for 120 minutes at ambient to reduce the Herceptin.

The contents of the reservoir and column were flushed to waste and replaced with PBS/EDTA/5% v/v DMA to which vcMMAE was added to give a molar ratio of 5 vcMMAE per mole of reduced Herceptin. This was allowed to recirculate for 60 minutes at ambient to conjugate the reduced Herceptin.

N-Acetyl cysteine (NAC) was added to quench unreacted vcMMAE and allowed to react for 20 minutes before the resin was washed sequentially with PBS/EDTA/5% v/v DMA and 0.1M glycine pH5.0.

The conjugates were eluted with 0.1M glycine pH 3.0. The eluted conjugates were collected into 2% v/v of 1M tris(hydroxymethyl)aminoethane (TRIS) to neutralise them.

The process was repeated in an independent second experiment using a second column/operator.

Figure 3:
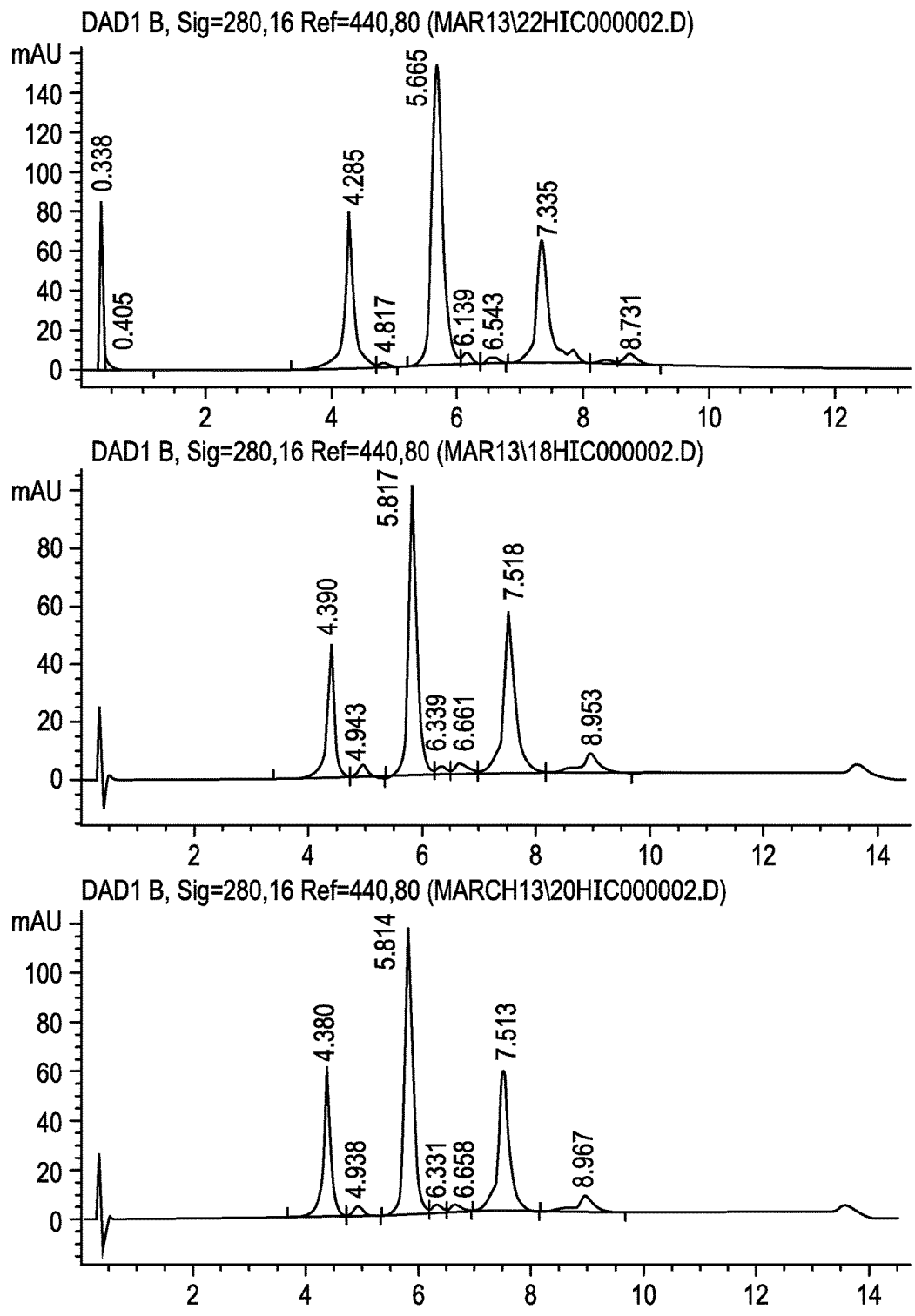
FIG. 3—HIC Analysis of Chromatographic Flow Solid Phase Herceptin vcMMAE Conjugates. HIC analysis of solution phase Herceptin vcMMAE conjugate (upper panel), Column A manufactured Herceptin vcMMAE (middle panel), Column B manufactured vcMMAE (lower panel).
Figure 4:
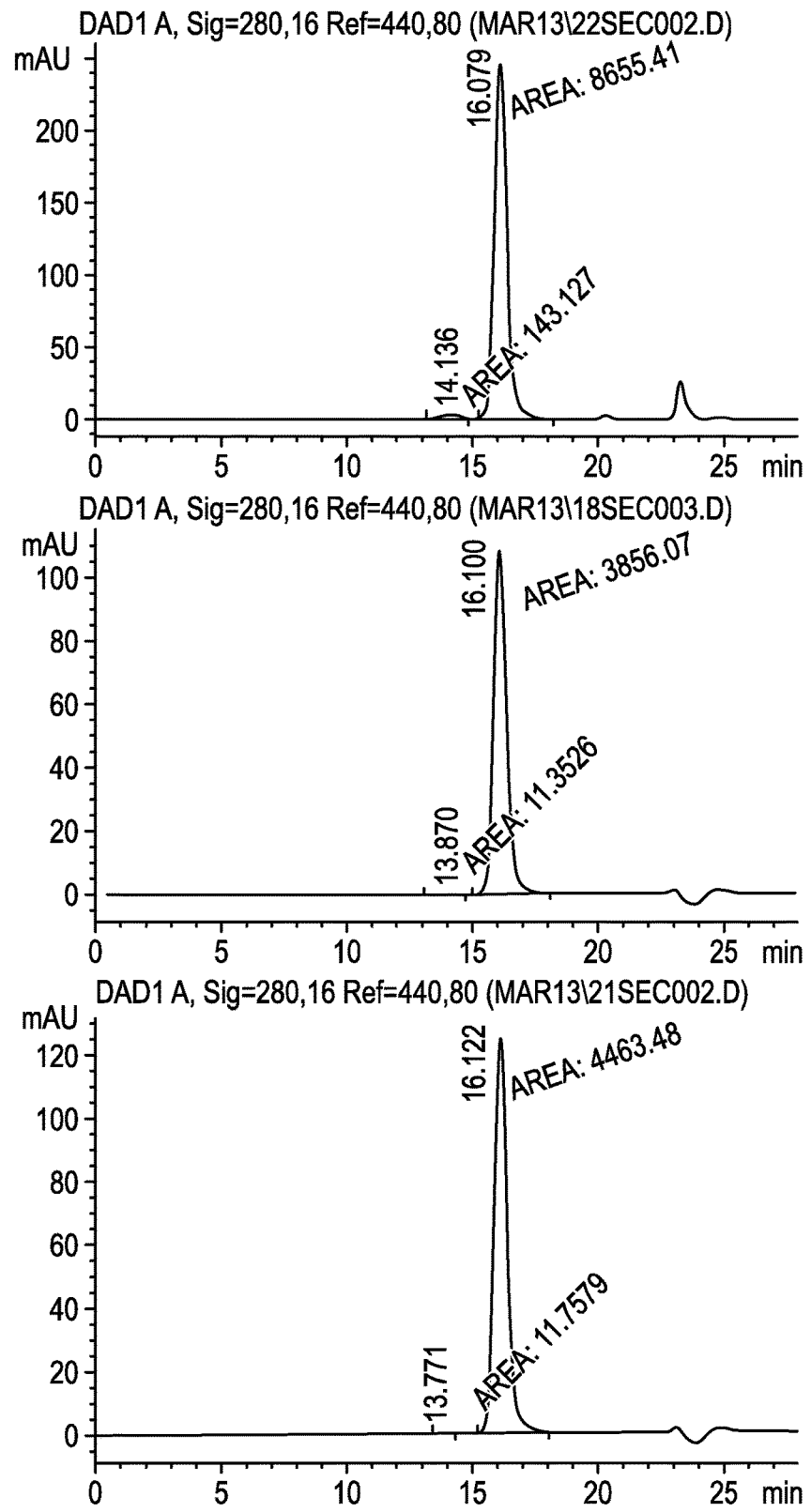
FIG. 4—SEC Analysis of Solid Phase Herceptin vcMMAE Conjugates. SEC analysis of solution phase Herceptin vcMMAE conjugate (upper panel), Column A manufactured Herceptin vcMMAE (middle panel), Column B manufactured vcMMAE (lower panel).
Figure 5:
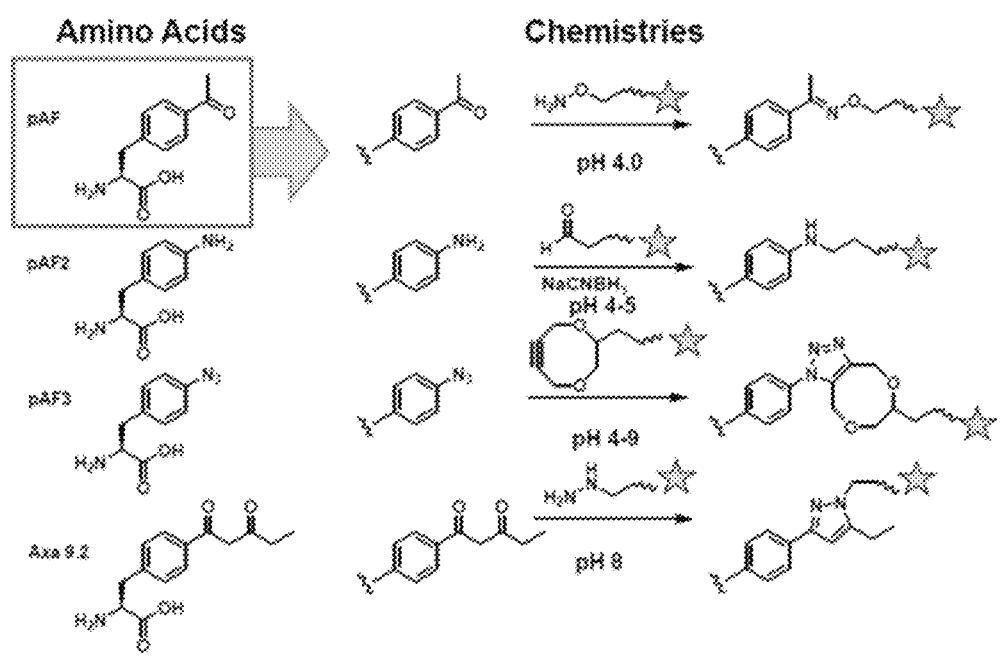
FIG. 5—Illustration of possible combination of orthogonal amino acid side chains and reactive chemistry (adapted from Ambryx presentation at Hanson Wade ADC summit meeting in February 2012).
Figure 6:
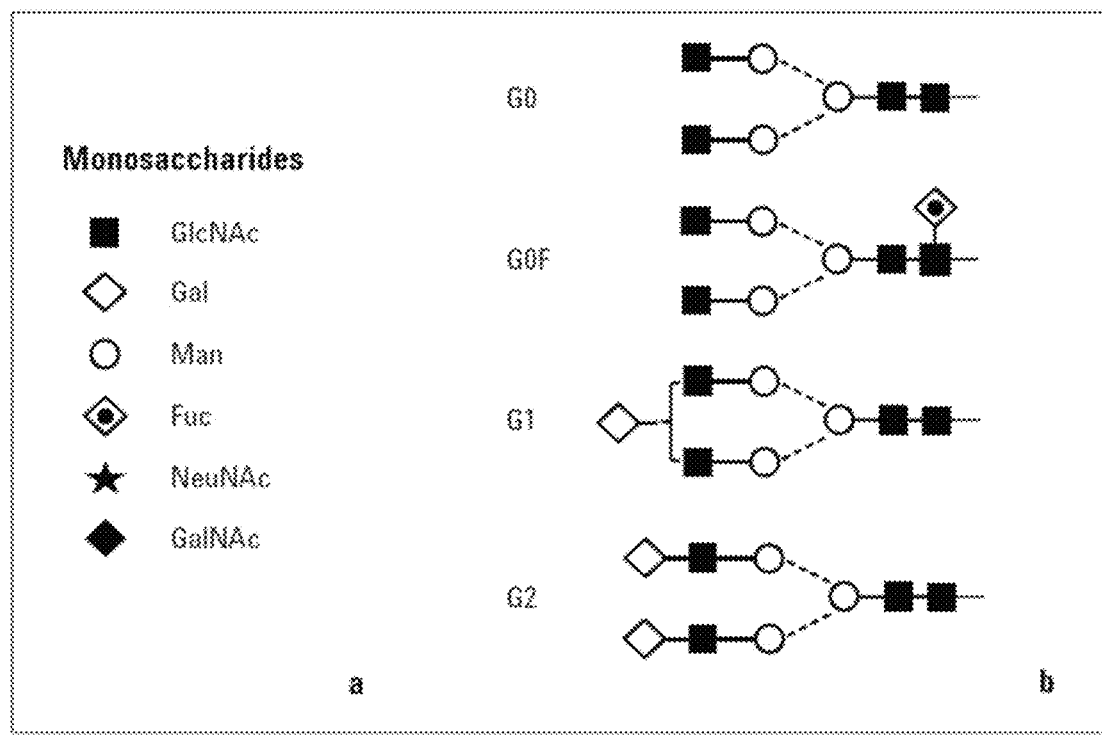
FIG. 6—Depiction of a typical antibody glycan structure to highlight the presence of mannose and galactose in antibody glycans (Adapted from Arnold et al, Advances in Experimental Medicine and Biology, 2005, 564, 27-43). Glycan structure and isoforms. A: General nomenclature for glycans; B: Predominant glycan structures of IgGs; G: Galactose units; and F: Fucose units.

The eluted conjugates were then analysed by Hydrophobic Interaction Chromatography (FIG. 3) and Size Exclusion Chromatography (FIG. 4) to determine the percentage aggregate and average drug loading.

The results are summarized in Table 3 below:

| Preparation Method | DAR | % Aggregate |
|---|---|---|
| Herceptin | 0 | 0.2 |
| Solution Phase | 2.4 | 0.6 |
| Column A | 2.4 | 0.3 |
| Column B | 2.4 | 0.3 |

The data shows that when adapted to a chromatographic flow mode the conjugation of vcMMAE to Herceptin is consistent with respect to average drug loading and aggregate generation. The DAR achieved in batch mode and chromatographic mode is the same when TCEP to antibody ratio is matched.

Example 4—Solid Phase Herceptin Conjugation with DM1 in Batch Mode Via SMCC Activation of Lysine Side Chains This example shows that immobilized antibodies can be conjugated on the side chain of lysine by modification with SMCC followed conjugation with DM1 and that product quality is enhanced relative to the same conjugates made in solution.

Herceptin (0.5 ml of 4 mg/ml PBS, pH7.4) was bound to 100 μl (settled resin volume) of Fabsorbant™ F1P HF resin equilibrated in PBS by mixing the resin slurry and antibody solution gently for 30 minutes. Unbound Herceptin was removed by washing the resin with PBS followed by 'Modification Buffer' (50 mM NaPi, 150 mM NaCl, 2 mM EDTA pH6.7) and the resin finally re-suspended in modification buffer containing 5% v/v DMA.

The bound Herceptin was modified by adding succinimidyl-4-(N-maleimidomethyl)cyclohexyl-1-carboxylate (SMCC) to a ratio of 5 to 20 moles of SMCC per mole of Herceptin and then incubating the suspension at ambient temperature for 4 hours. Unreacted SMCC was removed by washing the resin with PBS/5% v/v DMA followed by 'Conjugation Buffer' (35 mM sodium citrate, 150 mM NaCl, 2 mM EDTA pH5.0) and the resin finally re-suspended in conjugation buffer containing 3% v/v DMA.

DM1 was added to achieve 15 moles of DM1 per mole of Herceptin and the conjugation allowed to proceed for 18 hours at ambient. The resin was then washed sequentially with PBS/EDTA/5% v/v DMA and 0.1M glycine pH5.0.

The conjugates were eluted with 0.1M glycine pH3.0. The eluted conjugates was collected into 2% v/v of 1M tris (hydroxymethyl)aminoethane (TRIS) to neutralise them.

An equivalent solution phase conjugate of Herceptin with DM1 with matched DAR was produced by reacting Herceptin with 7.6 moles of SMCC followed by 5 moles of DM1 per mole of Herceptin and analysed to provide a comparison of solid phase and solution phase conjugate quality. The concentration of Herceptin during the modification and conjugation reactions was 10 and 5 mg/ml respectively.

The eluted conjugates were then analysed by Size Exclusion Chromatography and UV to determine the percentage aggregate and average drug loading.

The results are summarized in Table 4 below:

| Production Method | [Herceptin] during conjugation mg/ml | DAR | % Aggregate |
|---|---|---|---|
| Solution | 5 | 3.6 | 3.2 |
| Solid Phase | 20 | 1.7 | 1.8 |
| | | 2.6 | 2.8 |
| | | 3.5 | 3.0 |
| | | 4.8 | 3.5 |

The data shows that on solid supports lysine side-chain conjugation is possible and that the relationship between SMCC to antibody ratio and final drug loading is linear.

In addition when compared with an equivalent conjugate made in solution the solid phase conjugates show an equivalent percentage aggregation despite a four-fold increase in protein concentration during the conjugation reaction.

The invention claimed is:

1. A method of synthesising a biomolecule-drug-conjugate, the method comprising:
(i) contacting a biomolecule with FAbsorbent F1P HF resin, MAbsorbent A1P resin, MAbsorbent A2P resin, or a capture resin comprising a capture moiety for the biomolecule, wherein the capture moiety is:
a branched ligand scaffold of formula:

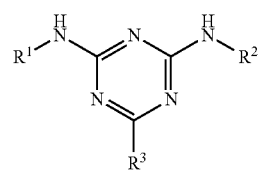

wherein $R^1$ and $R^2$ are the same or different and are each optionally substituted alkyl or aryl ligands, and $R^3$ is a solid support optionally attached by a spacer motif; or a branched triazyl scaffold of formula:

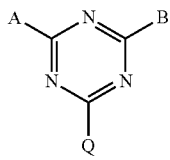

wherein Q represents the attachment point to a solid support matrix, optionally with a spacer motif and Groups A and B are phenyl or naphthyl groups substituted with one or more substituents capable of hydrogen bonding, optionally one or more of —OH, —SH and —CO$_2$H;

under conditions suitable to immobilise the biomolecule and therefore provide an immobilised biomolecule; wherein the biomolecule is an antibody, modified antibody or antibody fragment;

(ii) optionally contacting the immobilised biomolecule with a chemical modification agent or activating agent to provide a chemically modified or activated, immobilised biomolecule;

(iii) contacting the immobilised biomolecule or the chemically modified or activated, immobilised biomolecule with a drug component to form an immobilised biomolecule-drug-conjugate; and (iv) releasing the biomolecule-drug-conjugate from the capture resin.

2. The method of claim 1, wherein step (i) comprises incubating the biomolecule with the capture resin.

3. The method of claim 2, wherein the incubation is carried out at temperature of from about 10 to about 40° C., optionally from about 15 to about 37° C.

4. The method of claim 2, wherein the incubation is carried out for a period of time of about 10 minutes to about 18 hours.

5. The method of claim 2, wherein the incubation is carried out in a buffer solution, optionally phosphate buffered saline (PBS).

6. The method of claim 2, wherein the incubation is carried out at a pH of about 5 to about 8.

7. The method of claim 1, wherein after step (i) the immobilised biomolecule is washed to remove any biomolecule that has not been immobilised on the capture resin.

8. The method of claim 1, wherein step (ii) involves reducing the biomolecule.

9. The method of claim 8, wherein the biomolecule is reduced by contacting it with a reducing agent, optionally wherein the reducing agent is selected from the group consisting of tris(2-carboxyethyl)phosphine (TCEP), dithiothreitol (DTT), and merceptoethylamine.

10. The method of claim 1, wherein step (ii) involves reacting the biomolecule with a crosslinker moiety, optionally wherein the crosslinker moiety is succinimidyl 4-(N-maleimidomethyl)cyclohexane-1-carboxylate (SMCC).

11. The method of claim 8, wherein step (ii) is carried out in a buffer solution, optionally wherein the buffer is phosphate buffered saline (PBS).

12. The method of claim 8, wherein step (ii) is carried out at a pH of about 7 to about 8.

13. The method of claim 8, wherein step (ii) is carried out in the presence of a chelating agent, optionally wherein the chelating agent is EDTA.

14. The method of claim 8, wherein step (ii) involves incubating the biomolecule with the reducing agent for a period of time of about 6 hours to about 18 hours.

15. The method of claim 1, wherein after step (ii) the activated, immobilised biomolecule is washed to remove any modification/activating agent.

16. The method of claim 1, wherein step (iii) involves contacting the chemically modified or activated, immobilised biomolecule with a drug component in a buffer solution.

17. The method of claim 1, wherein step (iii) involves contacting the chemically modified or activated, immobilised biomolecule with a drug component at a pH of about 7 to about 8, optionally at a pH of about 7.4.

18. The method of claim 1, wherein step (iii) is carried out in the presence of a chelating agent, optionally wherein the chelating agent is EDTA.

19. The method of claim 1, wherein step (iii) involves incubating the chemically modified or activated, immobilised biomolecule with drug component for a period of time of about 6 hours to about 18 hours.

20. The method of claim 1, wherein after step (iii) the immobilised biomolecule-drug-conjugate is washed to remove any unreacted drug component.

21. The method of claim 1, wherein step (iv) involves altering the pH to break the support-biomolecule bond.

22. The method of claim 21, wherein the pH is decreased to less than about pH 5, optionally about pH 3.

23. The method of claim 21, wherein the eluted biomolecule-drug-conjugate is neutralised after the step of releasing the conjugate from the capture resin, optionally the conjugate is captured into 2% v/v of 1M tris(hydroxymethyl)aminoethane (TRIS).

24. The method of claim 1, wherein the ligand of the capture resin is represented by:

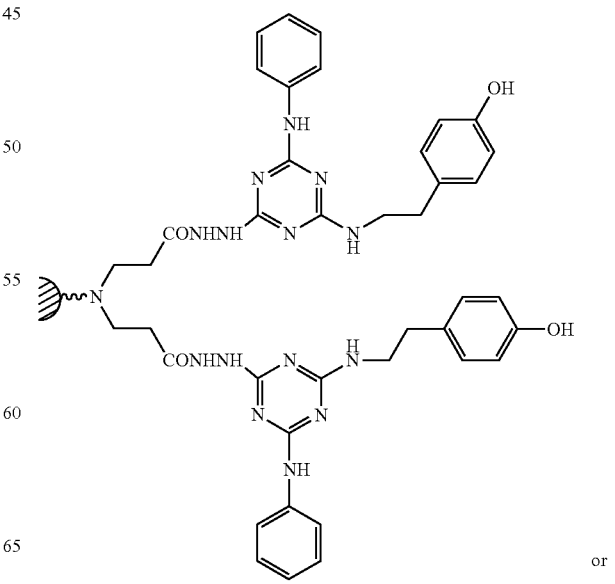

or

-continued

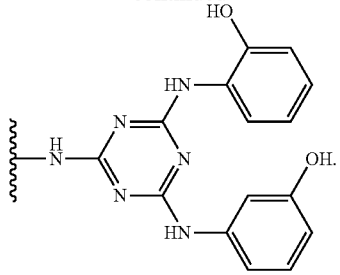

25. The method of claim 1, wherein the biomolecule is an antibody, optionally wherein the antibody is a monoclonal antibody and/or wherein the antibody is trastuzumab.

26. The method of claim 1, wherein the drug is a tubulin inhibitor or a DNA interacting agent; optionally wherein the tubulin inhibitor is selected from the group consisting of: (a) an auristatin; and (b) a maytansine derivative; optionally wherein the DNA interacting agent is selected from the group consisting of: (a) calicheamicins, (b) duocarmycins and (c) pyrrolobenzodiazepines (PBDs).

* * * * *